US012773549B2

(12) United States Patent
Zarins et al.

(10) Patent No.: US 12,773,549 B2
(45) Date of Patent: Oct. 27, 2026

(54) CRIMP TOOL FOR COMPRESSIBLE CATHETER PUMP

(71) Applicant: ABIOMED, Inc., Danvers, MA (US)

(72) Inventors: Christopher Zarins, Danvers, MA (US); Joerg Schumacher, Aachen (DE); Ralph D'Ambrosio, Danvers, MA (US); Thorsten Siess, Aachen (DE); Maxim Daschewski, Aachen (DE); Markus Birkhof, Aachen (DE); Daniel Roehn, Aachen (DE)

(73) Assignee: ABIOMED, Inc., Danvers, MA (US)

( * ) Notice: Subject to any disclaimer, the term of this patent is extended or adjusted under 35 U.S.C. 154(b) by 1039 days.

(21) Appl. No.: 17/848,113

(22) Filed: Jun. 23, 2022

(65) Prior Publication Data

US 2023/0009675 A1 Jan. 12, 2023

Related U.S. Application Data

(63) Continuation of application No. 17/563,373, filed on Dec. 28, 2021, now Pat. No. 12,558,529.

(Continued)

(51) Int. Cl.

*A61M 60/865* (2021.01)
*A61M 60/122* (2021.01)
*A61M 60/216* (2021.01)

(52) U.S. Cl.

CPC ........ *A61M 60/865* (2021.01); *A61M 60/122* (2021.01); *A61M 60/216* (2021.01); *A61M 2209/04* (2013.01)

(58) Field of Classification Search

CPC .............. A61M 60/865; A61M 60/122; A61M 60/216; A61M 2209/04

See application file for complete search history.

(56) References Cited

U.S. PATENT DOCUMENTS 3,799,492 A 3/1974 O'Laughlin
5,810,873 A 9/1998 Morales (Continued)

FOREIGN PATENT DOCUMENTS

CN 101336119 A 12/2008
CN 102481398 A 5/2012

(Continued)

OTHER PUBLICATIONS

International Search Report and Written Opinion for Application No. PCT/US21/65315 dated Apr. 22, 2022 (pp. 12).

(Continued)

*Primary Examiner* — Lindsey G Wehrheim

(74) *Attorney, Agent, or Firm* — BOTOS CHURCHILL IP LAW LLP

(57) ABSTRACT

A crimp tool facilitates crimping a resiliently radially compressible human-implantable catheter pump, and transferring the crimped pump into a tubular transfer sheath, by pulling the heart pump through an elongated tube that defines a tapered longitudinal bore. The bore has an inside dimension that tapers gradually along the length of the bore. A large end of the bore is sufficient to accept an uncrimped heart pump. A small end of the bore has a dimension similar to an inside dimension of the transfer sheath. A proximal end of the tube has a hub. A proximal end of a bore through the hub is configured to receive a distal end portion of the transfer sheath coaxially with the tube bore. Optionally, a latch is configured to releasably restrain the distal end portion of the transfer sheath within the hub.

19 Claims, 18 Drawing Sheets

Related U.S. Application Data

(60) Provisional application No. 63/275,264, filed on Nov. 3, 2021, provisional application No. 63/132,994, filed on Dec. 31, 2020.

(56) References Cited

U.S. PATENT DOCUMENTS

| | | | |
|---|---|---|---|
| 5,992,000 A | 11/1999 | Humphrey et al. | |
| 6,702,845 B1 | 3/2004 | Cully et al. | |
| 6,878,158 B2 | 4/2005 | Shin et al. | |
| 7,004,914 B2 | 2/2006 | Eberhart et al. | |
| 7,096,554 B2 | 8/2006 | Austin et al. | |
| 7,636,997 B2 | 12/2009 | Perreault et al. | |
| 7,854,188 B1 | 12/2010 | Buckley | |
| 7,878,967 B1 | 2/2011 | Khanal | |
| 8,439,859 B2 | 5/2013 | Pfeffer et al. | |
| 8,850,684 B2 | 10/2014 | Bregulla | |
| 8,893,370 B2 | 11/2014 | Hillukka et al. | |
| 8,973,234 B2 | 3/2015 | Johnson et al. | |
| 9,216,101 B2 | 12/2015 | State | |
| 9,393,112 B2 | 7/2016 | Tuval et al. | |
| 9,956,604 B1 | 5/2018 | Warriner et al. | |
| 11,638,644 B2 | 5/2023 | Taft et al. | |
| 2009/0093764 A1 | 4/2009 | Pfeffer et al. | |
| 2010/0049313 A1 | 2/2010 | Alon et al. | |
| 2010/0152523 A1 | 6/2010 | Macdonald et al. | |
| 2010/0262157 A1 | 10/2010 | Silver et al. | |
| 2012/0226096 A1 | 9/2012 | Callaway et al. | |
| 2013/0085318 A1 | 4/2013 | Toellner | |
| 2014/0255176 A1 | 9/2014 | Bredenbreuker et al. | |
| 2014/0331475 A1 | 11/2014 | Duffy et al. | |
| 2015/0141738 A1 | 5/2015 | Toellner et al. | |
| 2015/0360006 A1 | 12/2015 | Liu et al. | |
| 2016/0081785 A1 | 3/2016 | Dela | |
| 2017/0049947 A1 | 2/2017 | Corbett et al. | |
| 2018/0193611 A9 | 7/2018 | Joe et al. | |
| 2020/0237981 A1* | 7/2020 | Tuval | A61M 60/865 |
| 2020/0360581 A1 | 11/2020 | Scheckel | |
| 2023/0103353 A1 | 4/2023 | Aders et al. | |

FOREIGN PATENT DOCUMENTS

| | | |
|---|---|---|
| CN | 106512117 A | 3/2017 |
| CN | 111032113 A | 4/2020 |
| DE | 102006036948 A1 | 2/2008 |
| EP | 2399639 A1 | 12/2011 |
| JP | 2019535483 A | 12/2019 |
| JP | 2020531165 A | 11/2020 |
| KR | 20140037157 A | 3/2014 |
| WO | 2015160990 A1 | 10/2015 |
| WO | 2018094069 A1 | 5/2018 |
| WO | 2019038345 A1 | 2/2019 |

OTHER PUBLICATIONS

Mechanical Connecting Springs, Bal Seal Engineering, retrieved from the internet, https://www.balseal.com/spring/mechanical/, Oct. 4, 2020, copyright 2020, 12 pp., Oct. 4, 2020.

Edwards Lifesciences Services, GmbH, Edisonstr. 6, 85716 Unterschleissheim, Germany, Edwards SAPIEN 3 Kit—Transfemoral, Copyright 2016, released date Nov. 8, 2016, 9 pp., Nov. 8, 2016.

Shen, et al, Effect of Different Expansion Strategies on Coronary Stent Deployment in a Tapered Artery, Technology and Health Care 25 (2017) S21-S-28, School of Mech. Engineering, Jiangsu Univ., Zhenjiang, Jiangsu, China, 8 pp., 2017.

Hsiao, et al, Innovation of New Occlusion Devices for Cancers, Applied Sciences, 2017, 7, 530, Department of Mechanical Engineering, National Taiwan University, Taipel 10617, Taiwan; 14 pp., May 19, 2017.

Blockwise Engineering LLC, 425 S. 48th St., #108, Tempe, AZ 85281, Stent Crimper Model CX, retrieved from Internet, http://www.blockwise.com/stent-crimpers/cx/, Aug. 7, 2020, 12 pp., Aug. 7, 2020.

Blockwise Engineering LLC, Blockwise Knowledge Base AS205, Autosheath Film Selection, www.blockwise.com, 4 pp., Aug. 7, 2020.

Blockwise Engineering LLC, 425 S. 48th St., #108, Tempe, AZ 85281, LX—Stent Loading Machines, retrieved from internet, http://www.blockwise.com/stent-loaders/lx/, Aug. 7, 2020, 7 pp., Aug. 7, 2020.

Blockwise Engineering LLC, 425 S. 48th Street, #108, Tempe, AZ 85281, NJ—Stent Loading Machines, retrieved from the internet, http://www.blockwise.com/stent-loaders/nj/, Aug. 7, 2020, 7 pp., Aug. 7, 2020.

Puértolas, et al, Study of the Behavior of a Bell-Shaped Colonic Self-Expandable NiTi Stent under Peristaltic Movements, Dept. of Mech.I Eng., Univ. of Zaragoza, Maria de Luna 3, Zaragoza, Spain, Hindawi Pub. Corp., vol. 2013, Article ID 370582, 11 pp., May 21, 2013.

Garter Spring, Wikipedia, retrieved from the internet, https://en.wikipedia.org/wiki/Garter_spring, Oct. 4, 2020, 3 pp., Oct. 4, 2020.

Office action issued in Chinese Patent Application No. 2021800927453, dated Mar. 25, 2026 (13 pp.).

Office Action from corresponding Israeli Patent Application No. 303986 dated Nov. 2, 2025 (4 pp.).

Office Action from corresponding Japanese Patent Application No. 2023-539964 dated Nov. 4, 2025 (11 pp.).

Office Action from corresponding Taiwan Patent Application No. 110149109 dated Nov. 6, 2025 (14 pp.).

Office Action from corresponding Indian Patent Application No. 202317046766 dated May 27, 2026 (7 pp.).

Office action issued in Chinese Patent Application No. 2021800927453, dated Aug. 11, 2026 (14 pp.).

Office action issued in Korean Patent Application No. 10-2023-7022763, dated Jul. 30, 2026 (13 pp.).

Office Action from corresponding Japanese Patent Application No. 2023-539964 dated Jun. 23, 2026 (7 pp.).

* cited by examiner

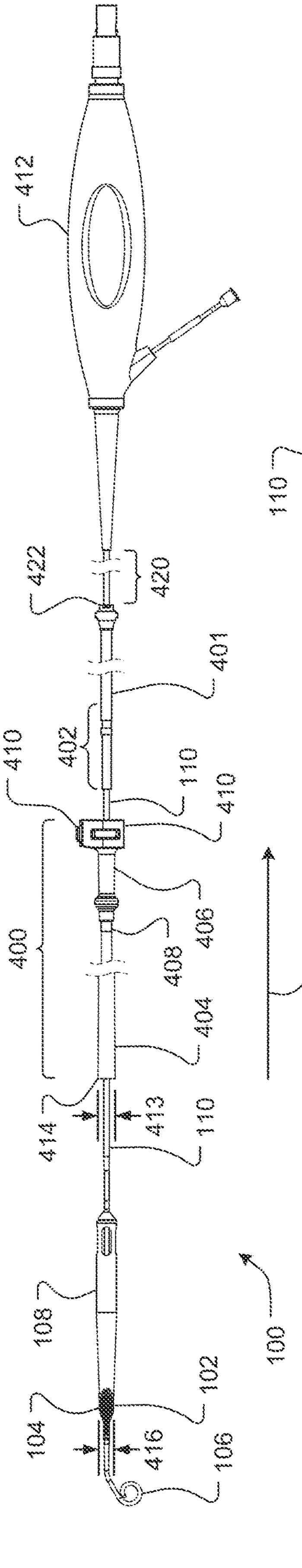
Fig. 4
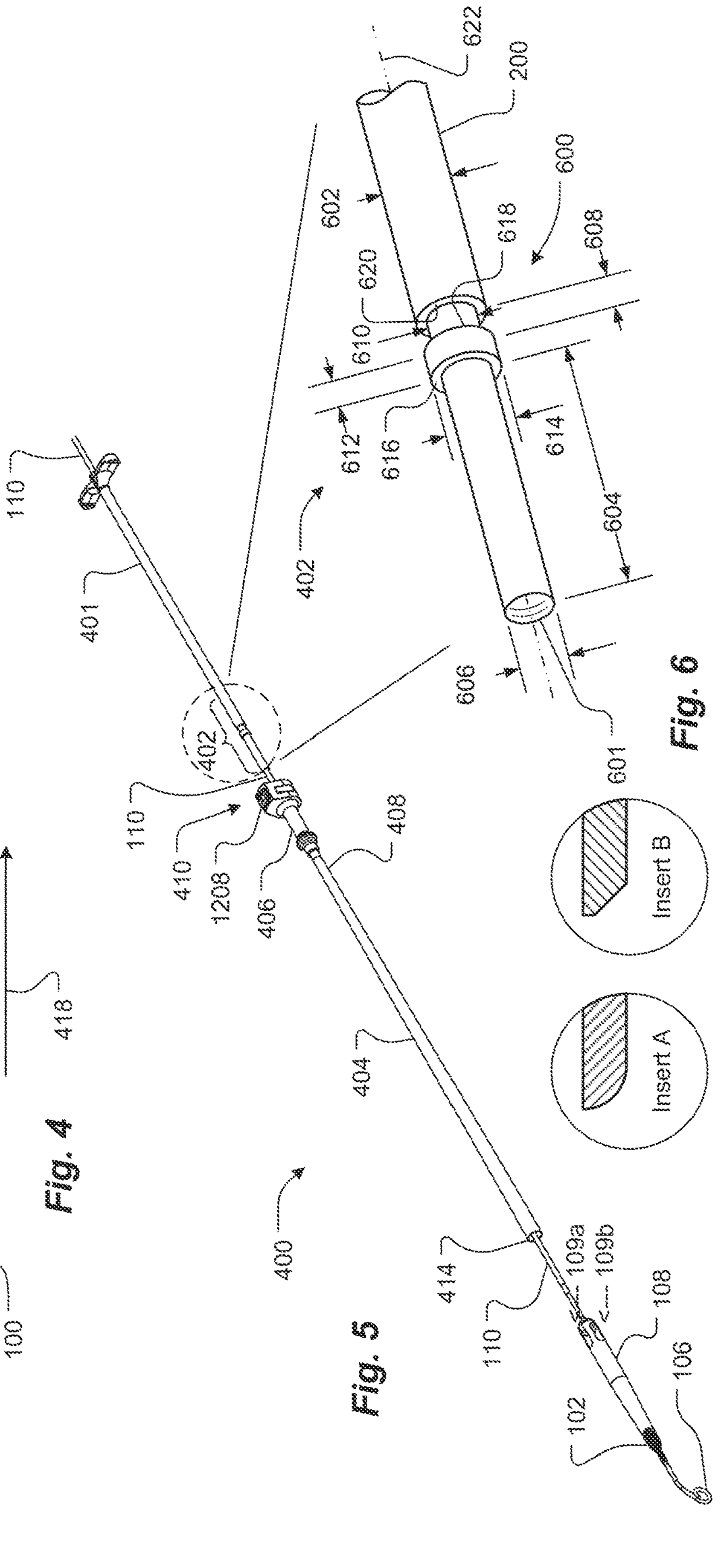
Fig. 5
Fig. 6

CRIMP TOOL FOR COMPRESSIBLE CATHETER PUMP

CROSS-REFERENCE TO RELATED APPLICATIONS

The present application is a continuation of U.S. patent Ser. No. 17/563,373, which was filed on Dec. 28, 2021 and claims priority from and the benefit of U.S. Provisional Application No. 63/132,994, which was filed on Dec. 31, 2020, and U.S. Provisional Application No. 63/275,264, which was filed on Nov. 3, 2021. All of which are incorporated by reference herein in their entirety.

BACKGROUND OF THE INVENTION

The present disclosure relates to tools for crimping transcatheter intravascular assist devices, and more particularly to tools for crimping expandable catheter blood pumps.

RELATED ART

An intravascular blood pump is a pump that can be advanced through a patient's blood circulatory system, i.e., veins and/or arteries, to a position in the patient's heart or elsewhere within the patient's vasculature. Such a blood pump is typically disposed at the end of a catheter, which is used to insert and position the pump, and later to withdraw the pump. Once in position, the pump may be used to pump blood through the circulatory system and, therefore, temporarily reduce workload on the patient's heart, such as to enable the heart to recover after a heart attack. An exemplary intravascular blood pump is available from Abiomed, Inc., Danvers, MA under the tradename Impella® heart pump.

Some intravascular blood pumps have resiliently radially-compressible ("crimpable") pump housings, and in some cases radially-compressible impellers, to facilitate inserting the pumps into patients. A compressible-housing blood pump is inserted into a patient while the blood pump and impeller are in compressed states, and then after the blood pump is properly positioned, the pump housing and the impeller are allowed to radially expand.

An exemplary compressible-housing blood pump is described in U.S. Pat. No. 8,439,859 ("the '859 patent"), the entire contents of which are hereby incorporated by reference herein, for all purposes. FIG. 8 of the '859 patent shows a tubular mesh structure of a pump housing. The tubular mesh structure may be made of a suitable memory material, such as nitinol. When radially compressed, the pump section of the tubular mesh structure may be about 3 mm in outside diameter. However, when unrestrained, the pump section resiliently rebounds to about 6.15 mm in outside diameter. Other compressible-housing blood pumps may have other compressed and/or rebounded outside diameters.

To prepare such a blood pump for insertion into a patient's vasculature, the blood pump must be radially compressed and then held in the compressed state, typically by inserting the compressed blood pump into a tubular transfer sheath. The transfer sheath is then attached to, or fed through, an introducer to insert the device into the patient's vein or artery. Once in the patient's vein or artery, and out of the transfer sheath or introducer, the blood pump housing radially resiliently expands.

Such a blood pump should be compressed shortly before inserting the blood pump into a patient, such as in a surgical suite minutes before insertion into the patient. Compressing the blood pump much earlier, such as during manufacture, is likely to negatively affect the blood pump's ability to resiliently rebound, because the resilient components may develop a memory of their compressed state.

Radially compressing the blood pump and inserting the compressed blood pump into the transfer sheath, without damaging the blood pump, is difficult, often requiring two highly skilled people working together. Conventional methods and apparatus used to compress blood pumps and insert the blood pumps into transfer sheaths involve several steps and precise alignment of several components, as well as significant training of the people involved. Simpler apparatus, and simpler and faster methods, for radially compressing a blood pump and inserting the compressed blood pump into a transfer sheath, without damaging the blood pump, would be highly desirable.

BRIEF SUMMARY OF THE INVENTION

A crimp tool for crimping a blood pump for transfer into a tubular sheath, the crimp tool is described herein. The crimp tool may have an elongated tube that defines a tapered longitudinal bore, the bore being at least about 30 mm long and having an inside dimension that tapers along the length of the bore from (a) at least about a maximum outside dimension of the pump at a distal end of the bore to (b) about an inside dimension of the tubular sheath at a proximal end of the bore. The crimp tool may have a hub attached to the proximal end of the tube, the hub defining a bore therethrough coaxial with the tube bore, one end of the hub bore being coupled to the proximal end of the tube bore, the other end of the hub bore being configured to receive a distal end portion of the tubular sheath substantially coaxially with the tube bore.

The crimp tool may have an inside dimension of the distal end of the tube bore that is at least about 7 mm. The inside dimension of the proximal end of the tube bore may optionally be at most about 4 mm. The inside dimension of the distal end of the tube bore may be at least about 7 mm, and the inside dimension of the proximal end of the tube bore may be at most about 4 mm.

The tube bore may be at least about 50 mm long. The tube bore may be at least about 100 mm long. The tube bore may be at least about 170 mm long. The tube bore may be at least about 300 mm long.

The crimp tool may have an inside wall of the tube that defines the tapered tube bore and extends at an angle, relative to a longitudinal axis of the tube, of less than about 2°. The tapered tube bore may have a taper ratio, calculated as a ratio of (a) a change in inside diameter of the tube bore to (b) length of the taper along a longitudinal axis of the tube is no greater than about 1:14.

The crimp tool may have a latch configured to releasably restrain the distal end portion of the tubular sheath within the other end of the hub bore. The latch may be disposed within the hub. The latch may have a first pillar, a second pillar and an actuator, the actuator being configured for activation by a human, the actuator having an inactivated mode and an activated mode. The first pillar may have an inactivated mode and an activated mode. The first pillar may be mechanically coupled to the actuator and configured to resiliently transition from the inactivated mode to the activated mode in response to activation of the actuator. The first and second pillars may collectively define an opening therebetween, the hub bore extending through the opening substantially coaxially with the tube bore. In the inactivated mode of the first pillar, a smallest dimension of the opening, as viewed along a longitudinal axis of the tube, may be smaller than in the activated mode of the first pillar. The first pillar may be configured to resiliently displace away from the second pillar, independently of activation of the actuator.

The crimp tool may have, in the inactivated mode of the first pillar, a smallest dimension of the opening, as viewed along a longitudinal axis of the tube, that is smaller than an outside dimension of a feature of the distal end portion of the tubular sheath. In the activated mode of the first pillar, the smallest dimension of the opening may be at least as large as the outside dimension of the feature.

In another aspect of the crimp tool, the second pillar may have an inactivated mode and an activated mode. The second pillar may be mechanically coupled to the actuator and configured to resiliently transition from the inactivated mode to the activated mode in response to activation of the actuator. In this aspect, the first and second pillars may be symmetric and each of the first and second pillars may have a first arcuate shape. In this aspect the respective concave sides of the first arcuate shapes may counterface each other and each of the first and second pillars may be configured to resiliently transition from its respective first arcuate shape to a second respective arcuate shape and may have a smaller radius in response to activation of the actuator. In such aspect, in the inactivated mode of the first and second pillars, the opening is more eccentric, as viewed along a longitudinal axis of the tube, than in the activated mode of the first and second pillar.

In a further aspect of the crimp tool each of the first and second pillars may have a front surface and a back surface. In this aspect the opening may extend from the front surfaces to the back surfaces to define a passage. The passage may be tapered to be narrower at the back surfaces than at the front surfaces.

In a further aspect the crimp tool latch may be disposed within the hub. The latch may have an actuator configured for activation by a human, the actuator having an inactivated mode and an activated mode. The latch may further have a radial spring mechanically coupled to the actuator and configured to resiliently increase an inside dimension in response to activation of the actuator. The latch may be disposed within the hub, and may have a threaded compression fitting.

In another aspect, described herein is a method for crimping a blood pump. According to one aspect of the method, the blood pump is disposed inside a distal end of a tapered longitudinal tube bore defined by an elongated tube, the tube bore being at least about 30 mm long and having an inside dimension that tapers along the length of the tube bore from (a) at least about a maximum outside dimension of the pump at the distal end of the tube bore to (b) at most about 4 mm in diameter at a proximal end of the tube bore. The blood pump is translated through the tube bore in a direction toward the proximal end of the tube bore, including contacting an outside surface of the blood pump with an inside surface of the elongated tube as the blood pump translates through the tube bore, thereby crimping the blood pump to produce a crimped blood pump.

In one aspect, translating the blood pump may be pulling the blood pump through the tube bore. The inside dimension of the distal end of the tube bore may be at least about 7 mm. The inside dimension of the proximal end of the tube bore may be at most about 4 mm. The inside dimension of the distal end of the tube bore may be at least about 7 mm, and the inside dimension of the proximal end of the tube bore may be at most about 4 mm. Optionally, the tube bore may be at least about 50 mm long. Further optionally, the tube bore may be at least about 100 mm long. Further optionally, the tube bore may be at least about 170 mm long. Further optionally the tube bore may be at least about 300 mm long.

In a further aspect of the method, an inside wall of the tube that defines the tapered tube bore extends at an angle, relative to a longitudinal axis of the tube, of less than about 2°. In yet another aspect, a taper ratio of the tapered tube bore, calculated as a ratio of (a) a change in inside diameter of the tube bore to (b) length of the taper along a longitudinal axis of the tube may be no greater than about 1:14.

According to a further aspect of the method, the tubular sheath is disposed substantially coaxially with the proximal end of the tube bore. The crimped blood pump is translated from the proximal end of the tube bore to the tubular sheath, without substantially altering an outside dimension of the crimped blood pump.

In another aspect of the method, the crimped blood pump is translated from the proximal end of the tube bore to the tubular sheath by: (a) releasably restraining a distal end portion of the tubular sheath in a hub, the hub being attached to the proximal end of the tube, the hub defining a hub bore therethrough coaxial with the tube bore, one end of the hub bore being coupled to the proximal end of the tube bore, the other end of the hub bore being configured to receive the distal end portion of the tubular sheath substantially coaxially with the tube bore. According to this aspect, the crimped blood pump is translated through the hub bore. According to this aspect of the method the distal end portion of the tubular sheath may be released from the hub.

In another aspect, the crimped blood pump may be translated out of the tubular sheath and into a vasculature of a patient. The crimped blood pump is allowed to resiliently expand within the vasculature.

In another aspect, the crimp tool has a tubular sheath that may have an inside dimension, an elongated tube that defines a tapered longitudinal tube bore, the tube bore being at least about 30 mm long and having an inside dimension that tapers along the length of the tube bore from (a) at least about a maximum outside dimension of the blood pump at a distal end of the tube bore to (b) about the inside dimension of the tubular sheath at a proximal end of the tube bore. The distal end of the tubular sheath may be coaxially and frangibly attached to the proximal end of the tube.

In another aspect, a method for crimping a blood pump is described in which the blood pump is disposed inside a distal end of a tapered longitudinal tube bore defined by an elongated tube. In this aspect, a proximal end of the tube may be coaxially and frangibly attached to a distal end of a tubular sheath that may have an inside dimension. The tube bore may be at least about 30 mm long and may have an inside dimension that tapers along the length of the tube bore from (a) at least about a maximum outside dimension of the blood pump at the distal end of the tube bore to (b) about the inside dimension of the tubular sheath at the proximal end of the tube bore. According to this aspect, the blood pump may be translated through the tube bore in a direction toward the proximal end of the tube bore, including contacting an outside surface of the blood pump with an inside surface of the elongated tube as the blood pump translates through the tube bore, thereby crimping the blood pump to produce a crimped blood pump. Further according to this aspect the crimped blood pump is translated from the proximal end of the tube bore to the tubular sheath, without substantially altering an outside dimension of the crimped blood pump. Further according to this aspect, the tubular sheath is frangibly detached from the tube, with the crimped blood pump disposed within the tubular sheath.

Also described herein is a system that may have a transfer sheath having a proximal end, a blood pump that may have a catheter with a retraction indicia arranged to aid during crimping of the blood pump and retraction of the blood pump into the transfer sheath; and a crimp tool arranged to crimp the blood pump. In this aspect of the system, when the crimped blood pump is seated in a desired position of the transfer sheath, the retraction indicia may be visible proximally of the proximal end of the transfer sheath. According to this aspect, the retraction indicia may include one or more bands extending around a circumference of a portion of the catheter, optionally wherein the retraction indicia may include an elongate band.

In another aspect, a system is described in which an introducer may be arranged to be received in a patient's vasculature. The system may have a blood pump having a catheter with an advancement indicia that may be arranged to aid during insertion of the blood pump through the introducer. The system may have a transfer sheath arranged to receive the blood pump, the transfer sheath having a proximal end. In this system, the advancement indicia may be visible proximally of the proximal end of the transfer sheath when the blood pump begins to emerge and/or has just emerged from the introducer.

In a further aspect of the system, the advancement indicia includes one or more bands extending around a circumference of a portion of the catheter, optionally wherein the retraction indicia includes an elongate band.

In another aspect, a method is described herein in which a blood pump is crimped using a crimp tool. The blood pump may have a catheter with a retraction indicia and an advancement indicia. According to the method, the crimped blood pump is retracted into a transfer sheath until the retraction indicia is visible proximally of the proximal end of the transfer sheath. In a further aspect of this method, the crimped blood pump is advanced into an introducer arranged to be positioned in a patient's vasculature until the advancement indicia is visible proximally of the proximal end of the transfer sheath.

BRIEF DESCRIPTION OF THE DRAWINGS

The present disclosure will be more fully understood by referring to the following Detailed Description of Specific Embodiments in conjunction with the Drawings, of which:

FIG. 4 is a side view of a crimp tool for crimping a resiliently radially compressible human-implantable catheter pump, such as the heart pump of FIGS. 1-2, and transferring the crimped pump into a tubular transfer sheath, according to an embodiment of the present disclosure.

FIG. 5 is a perspective view of a portion of FIG. 4.

FIG. 6 is an enlarged perspective view of a distal end portion of the transfer sheath of FIGS. 4 and 5 showing features of the distal end portion that may be engaged by an optional latch of the crimp tool, according to an embodiment of the present disclosure.

DETAILED DESCRIPTION

A crimp tool facilitates crimping a resiliently radially compressible human-implantable catheter pump, and transferring the crimped pump into a tubular sheath, by pulling the heart pump through an elongated tube that defines a tapered longitudinal bore. The bore has an inside dimension that tapers along the length of the bore, from (a) at least about a maximum outside dimension of the pump at a distal end of the bore, to (b) about an inside dimension of the tubular sheath at a proximal end of the bore. In some embodiments, a hub is attached to the proximal end of the tube. The hub defines a bore therethrough, coaxial with the tube bore. One end of the hub bore is coupled to the proximal end of the tube bore, and the other end of the hub bore is configured to receive a distal end portion of the tubular sheath substantially coaxially with the tube bore. Optionally, a latch is configured to releasably restrain the distal end portion of the tubular sheath within the other end of the hub bore. Several embodiments of the latch are described herein.

In some embodiments, the distal end portion of the tubular sheath is detachably attached to the proximal end of the tapered tube, such as by a frangible portion, without necessarily including a hub. In these embodiments, once the crimped pump is pulled into the tubular sheath, the frangible portion is broken to free the tubular sheath from the tapered tube.

Also described are: a peel-away sheath; and an introducer with a hub, similar to the hub of some embodiments of the crimp tool.

Definitions

As used herein, including in the claims, the term "resilient" means able to recoil or spring back into shape after deformation, such as bending, stretching or being compressed, by releasing energy stored internally as a result of the deformation.

As used herein, including in the claims, terms that denote shape, such as circle, circular or square, mean within reasonable manufacturing tolerances. Terms that denote relative position, such as coaxial or collinear, mean within reasonable manufacturing tolerances. Similarly, terms or phrases that denote dimensions, such as constant outside diameter along an object's length, mean within reasonable manufacturing tolerances.

As used herein, including in the claims, "tubular" does not necessarily mean having a circular cross section. A tubular item may, for example, have an oval, square or other shaped cross section.

Resiliently Radially-Compressible Blood Pump

Figure 1:
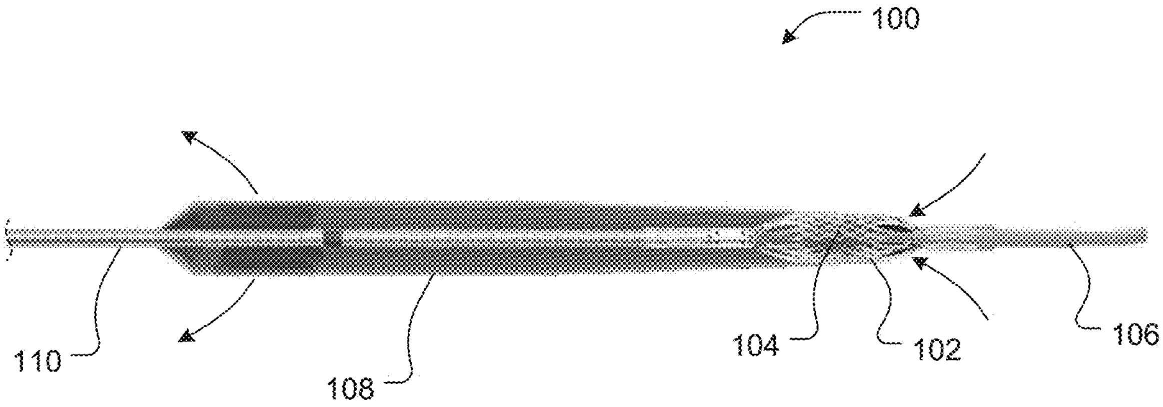
FIG. 1 is a side view of a resiliently radially-compressible intravascular blood pump.
Figures 7, 8:
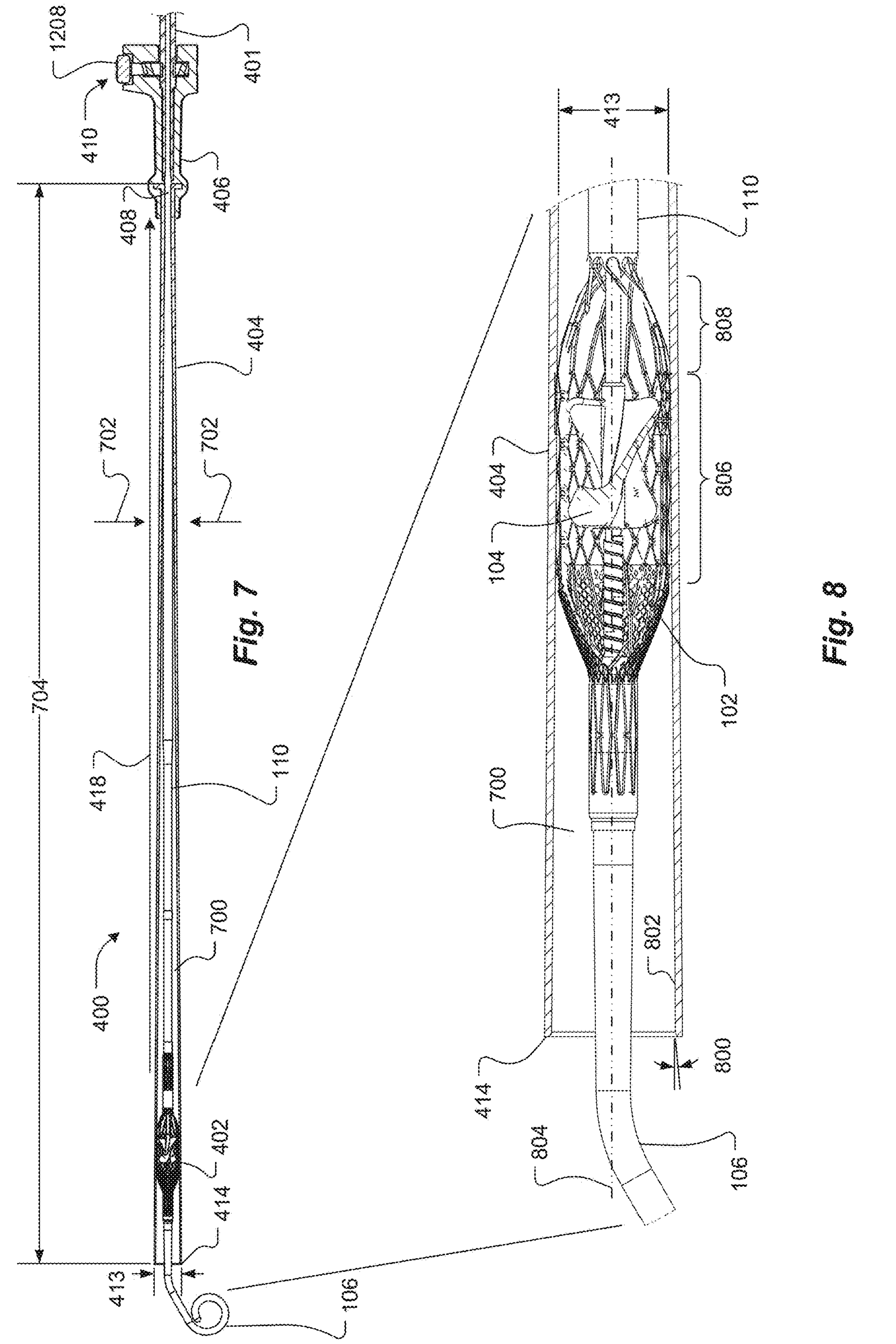
FIG. 7 is a cross-sectional view of the crimp tool of FIGS. 4-5, with the heart pump of FIGS. 1-2 partially pulled into a tube of the crimp tool, and the distal end portion of the transfer sheath of FIG. 6 inserted into a hub and restrained in the hub by the latch, according to an embodiment of the present disclosure.
FIG. 8 is an enlarged view of a distal portion of FIG. 7.

FIG. 1 is a side view of a resiliently radially-compressible intravascular blood pump 100, here shown in its uncompressed state. FIG. 8 provides an enlarged view of a portion of the blood pump 100. The blood pump 100 includes a tubular mesh structure 102 made of a suitable memory material, such as nitinol. An impeller 104 is disposed inside the tubular mesh structure 102. The impeller 104 may also be radially compressible, such as by folding resilient blades of the impeller 104. The blood pump 100 includes a resilient "pig tail" 106 (best seen in FIG. 1). The pig tail 106 may aid in positioning the blood pump 100 and/or avoiding damage to heart tissue, among other functions. The blood pump 100 may include a collapsible outflow tube 108 (best seen in FIG. 1). Blood flow into, and out of, the blood pump 100 is shown by arrows (FIG. 1). The blood pump 100 is attached to a distal end of a catheter 110.

Figure 2:
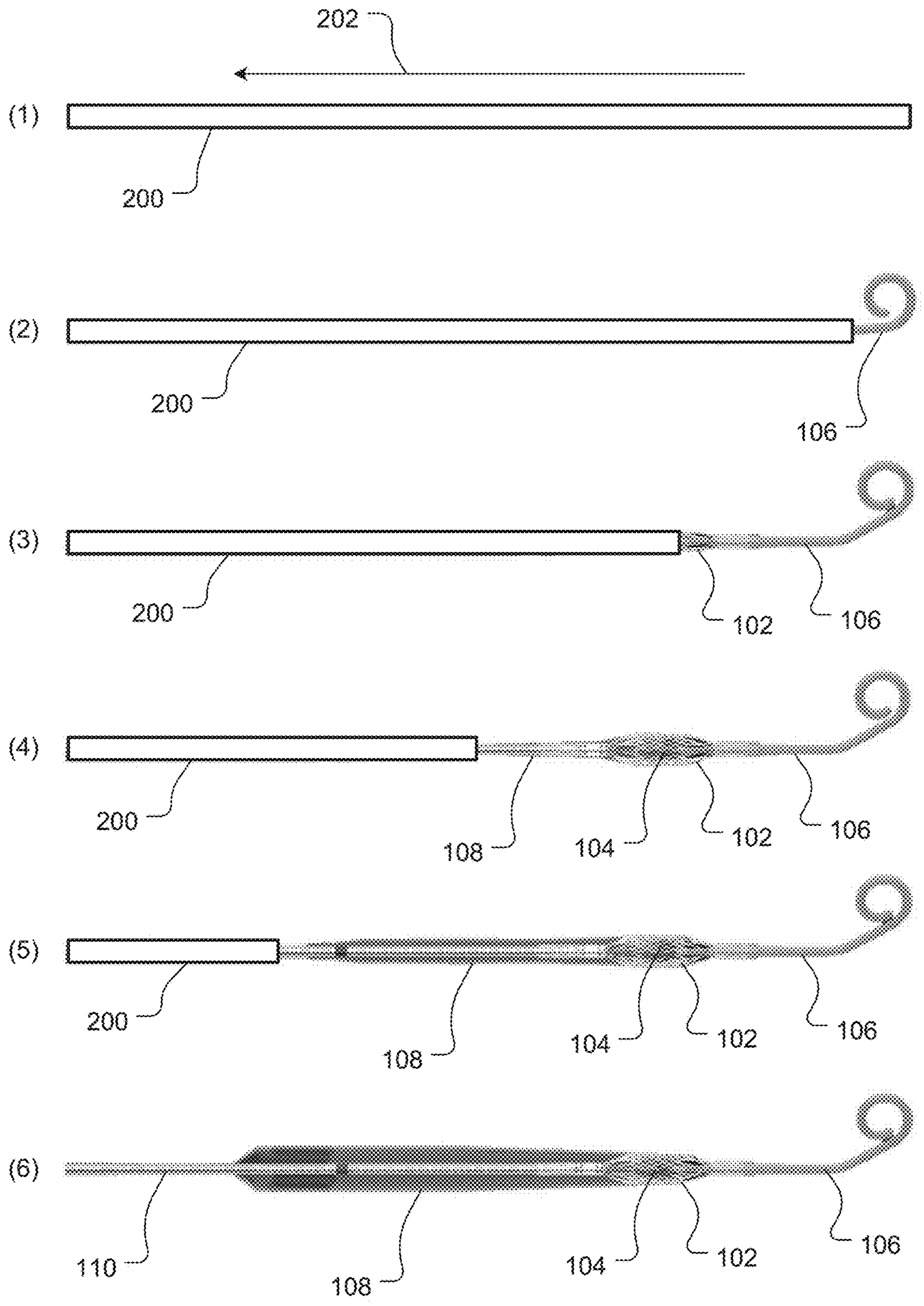
FIG. 2 is a side view of the blood pump of FIG. 1 in six stages ((1) to (6)) of emerging from a tubular sheath, as the sheath is withdrawn.

FIG. 2 is a side view of the blood pump 100 in six stages ((1) to (6)) of emerging from a tubular sheath 200, as the tubular sheath 200 is withdrawn, relative to the blood pump 100, as indicated by an arrow 202. As the tubular sheath 200 is withdrawn, portions of the blood pump 100, particularly the mesh structure 102 and the impeller 104, resiliently radially expand, and the pig tail 106 coils.

Conventional Crimping Tool

Figure 3:
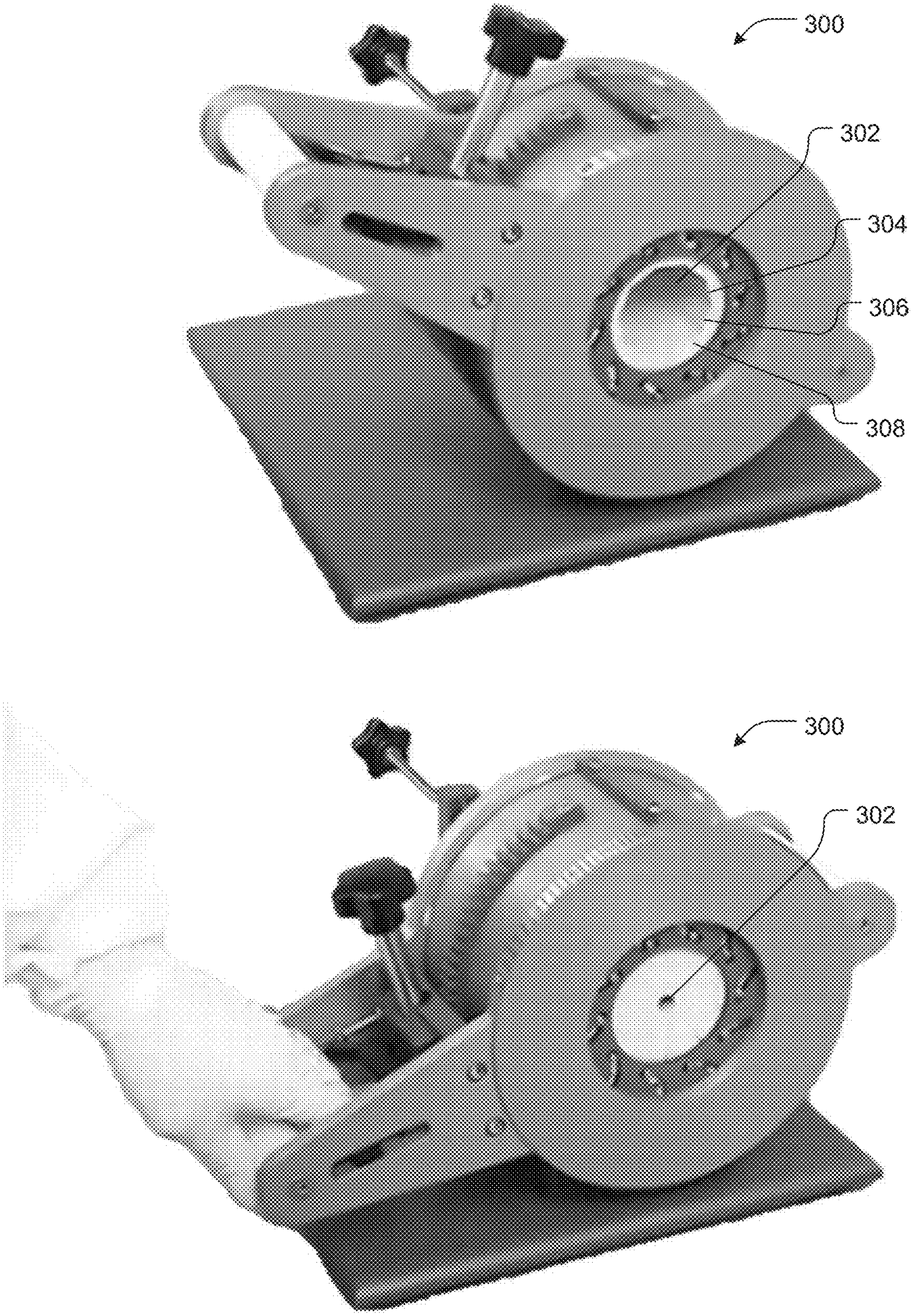
(Prior Art) Fig. 3
FIG. 3 is a perspective view of a conventional crimping tool, showing two stages of use thereof.

FIG. 3 is a perspective view of a conventional crimping tool 300 used to crimp stents and the like. The crimping tool 300 is shown in an open mode in the upper portion of FIG. 3, and in a closed mode in the lower portion of FIG. 3. The crimping tool 300 radially compresses an object placed in a chamber 302 of the crimping tool 300. The crimping tool 300 is large, heavy, complex, expensive and difficult to sterilize. Furthermore, the crimping tool 300 includes several radially disposed linear segments, represented by segments 304, 306 and 308, that collectively define the chamber 302. Thus, the chamber 302 is not circular in cross section. Instead, the chamber is a polygon in cross section. Consequently, an object crimped by the crimping tool 300 may be undesirably distorted or damaged by the segments 304-308 or by corners formed at intersections of adjacent pairs of the segments 304-308.

Crimp Tool

FIG. 4 is a side view of a crimp tool 400 for crimping a resiliently radially compressible human-implantable catheter pump 100 and transferring the crimped pump 100 into a tubular sheath, represented by a tubular transfer sheath 401, according to an embodiment of the present disclosure. The transfer sheath 401 has certain physical features, which are described herein with respect to FIG. 6. However, the crimp tool 400, or a suitable variation thereof, can be used with other tubular sheaths, such as tubular sheaths that lack these features. FIG. 5 is a perspective view of a portion of FIG. 4. FIG. 6 is an enlarged perspective view of a distal end portion 402 of the transfer sheath 401. Insert A and Insert B are respective close-up cross-sectional views of an extreme distal end portion 601 of the transfer sheath 401, according to respective embodiments.

Main components of the crimp tool 400 include: an elongated tube 404 that defines a tapered longitudinal bore, and a hub 406 attached to a proximal end 408 of the tube 404. The tube 404 and the hub 406 may be separate components jointed together, such as by a mechanical interlock, threaded connection, compression fitting, ultrasonic weld, adhesive or other suitable joint. Alternatively, the tube 404 and the 406 may be made as a single integrated component. In either case, the tube 404 and the hub 406 may be made of the same material or different materials. Although the tube 404 is shown as being straight in FIG. 4, the tube 404 may curve, such as due to manufacturing non-idealities or weight of the tube 404 and flexibility of the material from which the tube 404 is made. Optionally, the tube 404 may be coiled or made with an inherent curve, so the coiled or curved tube 404 fits more easily into its packaging (not shown).

Optionally, the crimp tool 400 includes a latch 410. If present, the latch 410 is configured to releasably restrain the distal end portion 402 of the transfer sheath 401. In the embodiment shown in FIGS. 4 and 5, the latch 410 is disposed within the hub 406, but in another embodiment, a suitable latch may be external to the hub 406.

Tube

A taper angle of the longitudinal bore of the tube 404 is relatively small, as described herein, to gradually compress (crimp) the heart pump 100, as the heart pump is pulled through the crimp tool 100, without damaging the heart pump 100. For example, some heart pumps pulled through some embodiments of the crimp tool 400 are not materially longitudinally distorted. In other examples, the tubular mesh structure 102 (FIG. 1) and/or the impeller 104 may be resiliently longitudinally lengthened, but without damaging the tubular mesh structure 102 or the impeller 104. That is, once the crimped heart pump 100 is withdrawn from the transfer sheath 401, the crimped portions of the heart pump 100 resiliently rebound to substantially their pre-crimped size and shape.

FIGS. 4 and 5 show a heart pump 100 in position, ready to be crimped by the crimp tool 400. In particular, the catheter 110 extends through the tapered longitudinal bore of the tube 404 and through the hub 406 to a handle 412. The tube 404 has an inside dimension 413 that tapers along the length of the bore, from a maximum inside dimension at a distal end 414 of the tube 404, to a smaller inside dimension at the proximal end 408 of the tube 404. In some embodiments, the inside dimension 413 tapers monotonically along the length of the bore. Some embodiments include non-tapered portions of the bore. Some embodiments include counter-tapered portions of the bore. In some embodiments, the inside dimension 413 smoothly tapers, whereas in other embodiments, the inside dimension 413 is stepped.

At the distal end 414 of the tube 404, the inside dimension 413 of the tube 404 is at least as large as about a maximum outside dimension 416 of the heart pump 100, to admit the blood pump 100 into the tube 404, without substantially radially crimping the blood pump 100. In other words, the inside dimension 413 is at least 80% of the dimension 416 of the heart pump 100. In some embodiments, the inside dimension 413 is at least about 100% of the dimension 416 of the heart pump 100. In some embodiments, the inside dimension 413 is at least about 110% of the dimension 416 of the heart pump 100. In some embodiments, the inside dimension 413 is at least about 120% of the dimension 416 of the heart pump 100. In some embodiments, the inside dimension 413 is at least about 130% of the dimension 416 of the heart pump 100. In some embodiments, the inside dimension 413 is at least about 150% of the dimension 416 of the heart pump 100. In some embodiments, the inside dimension 413 is at least about 200% of the dimension 416 of the heart pump 100.

The cross-sectional shape of the distal end 414 opening into the tube 404 should be similar to the cross-sectional shape of the compressible portion of the heart pump 100. In most embodiments, the cross-sectional shape of the inside of the tube 404 is circular or nearly circular. In some cases, the cross-sectional shape of the inside of the tube 404 is slightly oval, for example due to manufacturing non-idealities. Although the tubular mesh structure 102 (FIG. 1) of the blood pump 100 may be made of struts and therefore give the tubular mesh structure 102 a polygonal cross-sectional shape, which approximates a circular shape, we refer to the cross-sectional shape of such a tubular mesh structure 102 as circular. In other embodiments, the cross-sectional shape of the inside of the tube 404 is approximately square, approximately rectangular or another suitable shape.

The "maximum outside dimension 416 of the heart pump" 100 refers to a portion of the heart pump 100 that requires careful crimping, for example the tubular mesh structure 102. If, for example, the collapsible outflow tube 108 is non-rigid plastic that collapses by itself when not under internal pressure, the collapsible outflow tube 108 may not require careful crimping. In this case, the outside dimension of the collapsible outflow tube 108 is not considered to define the maximum outside dimension 416 of the heart pump 100. In respective embodiments, the inside dimension 413 of the distal end 414 of the tube 404 bore is at least about 7 mm, at least about 8 mm, at least about 10 mm, at least about 15 mm or at least about 30 mm. In other embodiments, the inside dimension 413 of the distal end 414 of the tube 404 bore is selected based on a dimension and/or cross-sectional shape of an intended heart pump 100.

The cross-sectional shape of the proximal end 408 opening of the tube 404 should be similar to the cross-sectional shape of the opening of the transfer sheath 401. In most embodiments, the cross-sectional shapes are circular or nearly circular. In some cases, the cross-sectional shape of the inside of the tube 404 is slightly oval, due to manufacturing non-idealities, or to accommodate asymmetric radial, such as slightly non-circular, compression of the rotor blades. The dimensions and sizes should be about the same, so the compressed heart pump 100 can easily transition from the proximal end 408 of the tube 404, into the transfer sheath 401. In this context, "same" means within manufacturing tolerances.

At the proximal end 408 of the tube 404, the inside dimension 413 of the tube 404 is about the same as an inside dimension of the transfer sheath 401. In respective embodiments, the inside dimension 413 of the proximal end 408 of the tube 404 bore is at most about 4 mm, at most about 3 mm, at most about 2 mm or at most about 1.5 mm. In some embodiments, the inside dimension 413 of the proximal end 408 of the tube 404 bore is about 0.1 to about 0.3 mm smaller than the inside dimension of the transfer sheath 401. In some embodiments, the inside dimension 413 of the proximal end 408 of the tube 404 bore is selected based on dimensions and/or cross-sectional shape of an intended heart pump 100.

In some embodiments, the inside dimension 413 of the proximal end 408 of the tube 404 bore is about 0.1 to about 0.3 mm larger than the inside dimension of the transfer sheath 401. In these cases, the extreme distal end portion 601 of the transfer sheath 401 should be rounded or chamfered, as shown in FIG. 6, Insert A and Insert B, respectively.

Optionally, the cross-sectional shape of the distal end 414 opening into the tube 404 may be different from the cross-sectional shape of the proximal end 408 opening of the tube 404, for example to match the cross-sectional shape of the opening of the transfer sheath 401. In these cases, the cross-sectional shape of the bore gradually changes along the length of the bore to smoothly transition from the distal end 414 opening cross-sectional shape to the proximal end 408 opening cross-sectional shape.

The tube 404 may be made of an extruded polymer material, such as polytetrafluoroethylene (PTFE). Alternatively, the tube 404 may be made of polyether block amide (PEBA), polyethylene, including high-density polyethylene (HDPE) or low-density polyethylene (LDPE), nylon, polypropylene (PP), polyoxymethylene (POM) or another suitable material. For example, PebaSlix® medical tubing, available from Duke Extrusion, Santa Cruz, CA is suitable. Optionally or alternatively, the material of the tube 404 may include an additive, or the inside surface of the tube 404 may be coated with PTFE or another suitable substance, to reduce friction. In any case, the inside surface of the tube 404 should be smooth and have a relative low coefficient of friction, relative to the outer materials of the heart pump 100.

Thus, when pulled through the tube 404, as indicated by an arrow 418, the heart pump 100 is gradually radially compressed, and optionally changed in cross-sectional shape, by the inside wall(s) of the tube 404, until the compressed heart pump 100 fits inside the transfer sheath 401.

FIG. 7 is a cross-sectional view of the crimp tool 400, with the heart pump 100 partially pulled into the tube 404, and the distal end portion 402 of the transfer sheath 401 inserted into the hub 406 and restrained in the hub 406 by the latch 410. A portion of the pigtail 106 remains outside the tube 404, not yet having been pulled into the tube 404. FIG. 8 is an enlarged view of a portion of FIG. 7.

As can be seen in FIGS. 7 and 8, in this embodiment, the inside dimension 413 of the tube 404 monotonically tapers along the length of the tube bore 700, from at least about the maximum outside dimension 416 (FIG. 4) of the heart pump 100 at the distal end 414 of the tube bore 700, to about an inside dimension of the transfer sheath 401 at the proximal end 408 of the tube bore 700. An inside edge of the distal end 414 of the tube 404 may be chamfered or rounded, to prevent damage to components of the blood pump 100, such as the outflow tube 108, as the blood pump 100 enters the tube bore 700.

Hub

Figure 10:
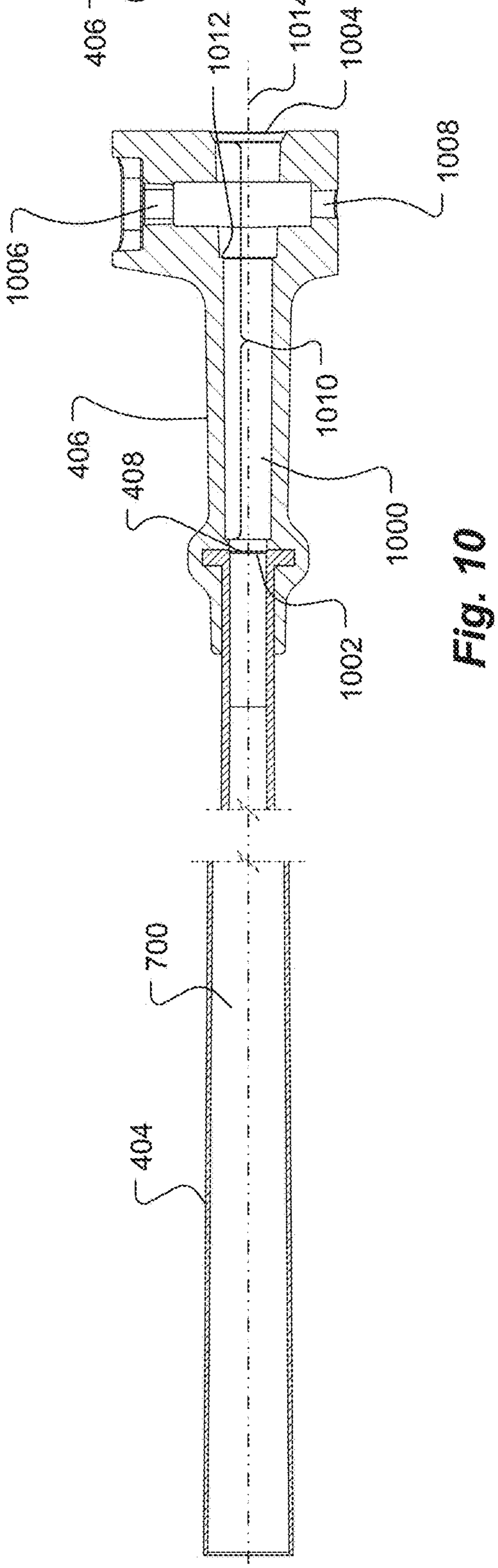
FIG. 10 is a cross-sectional view of the crimp tool of FIGS. 4-5, similar to FIG. 7, but absent the heart pump of FIGS. 1-2 and absent the latch of FIG. 7 for clarity, according to an embodiment of the present disclosure.

FIG. 10 is a cross-sectional view of the crimp tool 400, similar to FIG. 7, but absent the heart pump 100 and absent the latch 410, for clarity. The hub 406 defines a hub bore 1000 therethrough. The hub bore 1000 is coaxial with the tube bore 700. One end 1002 of the hub bore 1000 is coupled to the proximal end 408 of the tube bore 700. The other end 1004 of the hub bore 1000 is configured to receive the distal end portion 402 of the transfer sheath 401 approximately coaxially with the tube bore 700, as discussed in more detail herein, with respect to FIG. 17.

Thus, holding the hub 406 in one hand, and pulling the handle 412 or the catheter 110 at a location 420 (FIG. 4) between a proximal end 422 of the transfer sheath 401 and the handle 412 with another hand, a user pulls the heart pump 100 into, and then through, the tapered longitudinal bore 700 of the tube 404, and then through the hub 406, into the transfer sheath 401. As the heart pump 100 translates through the tapered longitudinal bore 700 of the tube 404, the heart pump 100 is gradually radially compressed (crimped), as indicated by arrows 702 (FIG. 7), without damaging the mesh structure 102 or the impeller 104. The transfer sheath 401 may then be released from the hub 406 by activating the latch 410, as discussed in more detail herein, and the transfer sheath 401, with the compressed heart pump 100 disposed therewithin, may then be withdrawn from the hub 406.

In some embodiments, the distal end portion 402 of the transfer sheath 401, with the compressed heart pump 100 disposed therewithin, is coupled to an introducer sheath (not shown), and the compressed heart pump 100 is then pushed through the introducer sheath into a patient's vasculature, where the heart pump 100 expands. In some embodiments, the transfer sheath 401, with the compressed heart pump 100 disposed therewithin, is itself passed through an introducer sheath (not shown) into the vasculature, and then the compressed heart pump 100 is pushed out of the transfer sheath 401 into a patient's vasculature, where it expands. In the latter case, the transfer sheath should have a smooth outer surface, rather than define a mechanical feature such as feature 600, to avoid thrombogenic issues. Thus, such embodiments are better matched with a compression latch, such as described herein with respect to FIG. 30.

The taper angle 800 (exaggerated for clarity in FIG. 8) is measured between an inside wall 802 of the tube 404 and a line parallel to the longitudinal axis 804 of the tube 404. That is, the inside wall 802 of the tube 404 that defines the tapered tube bore 700 extends at the taper angle 800, relative to the longitudinal axis 802 of the tube 404. As noted, the tube 404 may be curved, rather than perfectly straight. In these cases, the longitudinal axis 804 is also curved, and the taper angle 800 is measured relative to a line parallel to the longitudinal axis 804 at a cross section that is transverse to the longitudinal axis 804 and extends through the tube wall at the taper angle 800 measurement point. As noted, the taper angle 800 of the longitudinal bore 700 of the tube 404 is relatively small, to gradually compress (crimp) the heart pump 100, as the heart pump 100 is pulled through the crimp tool 100, without damaging the heart pump 100. In respective embodiments, the taper angle 800 is less than about 0.5°, less than about 0.6°, less than about 0.7°, less than about 1° or less than about 2°. In other embodiments, the taper angle 800 can have other upper limits, but generally less than about 10°.

Alternatively, the taper of the longitudinal bore 700 may be expressed as a taper ratio, calculated as a ratio of: (a) a change in inside diameter 413 of the tube bore 700 to (b) length 704 of the taper along the longitudinal axis 804 of the tube 404. In respective embodiments, the taper ratio is no greater than about 1:14, no greater than about 1:20, no greater than about 1:30, no greater than about 1:40, no greater than about 1:50, no greater than about 1:60 or no greater than about 1:70.

In some embodiments, the tube bore 700 is at least about 30 mm long. In some embodiments, the tube bore 700 is at least about 50 mm long. In some embodiments, the tube bore 700 is at least about 100 mm long. In some embodiments, the tube bore 700 is at least about 170 mm long. In some embodiments, the tube bore 700 is at least about 300 mm long.

The length of the tube bore 700 and the taper angle 800 (alternatively, taper ratio) should be chosen such that crimping forces experienced by the impeller 104 are largely or exclusively radial, and such that the impeller 104 experiences no or little longitudinal force. In general, these objectives can be met when the inside wall(s) of the tube 404 contact only a cylindrical portion 806 (FIG. 8) of the mesh structure 102, and when the inside wall(s) of the tube 404 do not contact, or minimally contact, a proximal curved portion 808 of the mesh structure 102. Alternatively, in general, these objectives can be met when the taper angle 800 is selected such that the inside wall(s) of the tube 404 contact the pump housing at, or close to, its maximum outside diameter and near the impeller. In part, geometry of the tube bore 700 may depend at least in part on axial position of the impeller 104 within the mesh structure 102.

Figure 9:
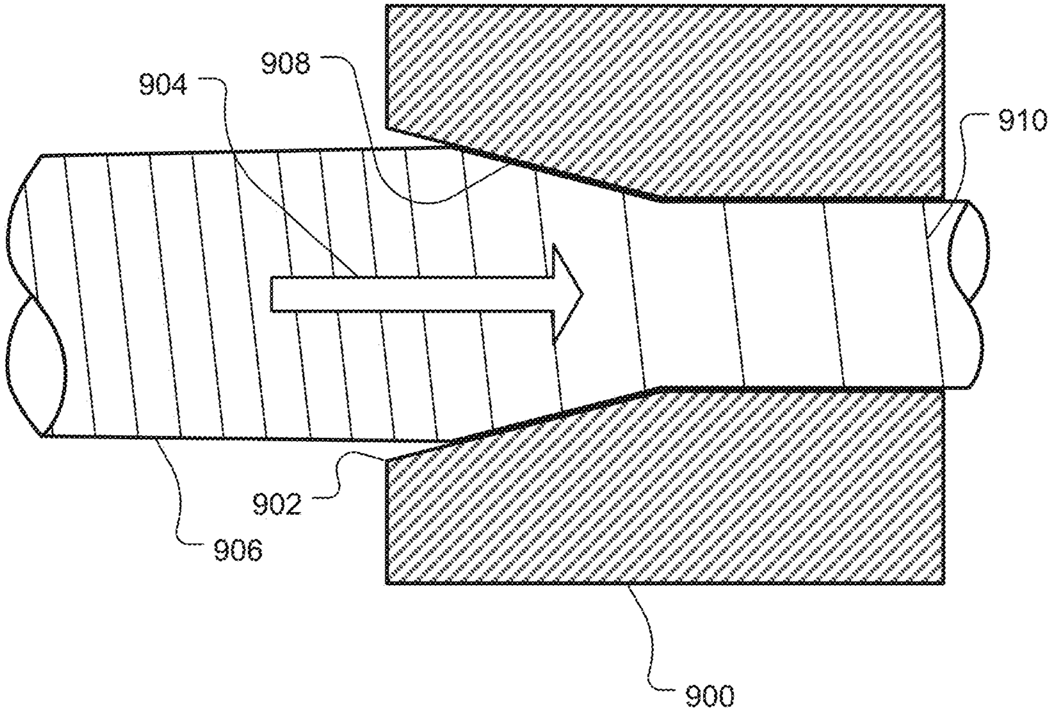
(Prior Art) Fig. 9
FIG. 9 is a cross-sectional view of a conventional die.

The tube 404, with its tapered bore 700, is, however, distinguishable from a die, such as a wire drawing die. FIG. 9 is a cross-sectional view of an exemplary conventional die 900. A die is a conventional material-shaping device that defines an aperture, exemplified by aperture 902, through which to pull (draw, as indicated by arrow 904) an object, exemplified by wire 906, in order to reduce a cross-sectional dimension of the object to a dimension of the aperture 902. The aperture 902 may be tapered, as indicated at 908. However, as a result of the drawing, the length of the object 906 necessarily increases, as indicated by increased spacing between hatch marks 910. The length increases, because the object 906 is solid and essentially incompressible, not resilient like a radially-compressible blood pump 100. Furthermore, conventional wire drawing die tapers 908 are much steeper than the taper angle 800 or the taper ratio described herein.

As the object 906 is pulled through the die 900, the wire's volume remains the same. Therefore, as the diameter of the wire decreases, the length of the wire 906 necessarily increases. Furthermore, the process of wire drawing changes material properties of the wire, due to cold working.

In contrast, the crimp tool 400 described herein radially resiliently compresses (crimps) a heart pump 100, without damaging the heart pump 100, due to the gradual taper of the tube 404. In essence, the crimp tool 400 decreases the volume of the heart pump 100, unlike a wire drawing die.

Optional Latch

As noted with reference to FIG. 7, the crimp tool 400 optionally includes a latch 410 to releasably restrain the distal end portion 402 of the transfer sheath 401 in the hub 406. FIG. 6 is an enlarged perspective view of a distal end portion 402 of the transfer sheath 401, showing a mechanical feature 600 that may be engaged by the latch 410 to releasably restrain the distal end portion 402 in the hub 406. The latch 410 is configured to resiliently deform in response to the feature 600 of the distal end portion 402 of the transfer sheath 401 entering the latch 410. The latch 410 is further configured to at least partially rebound, as the feature 600 is further inserted into the latch 410, to mechanically capture the feature 600, to restrain the distal end portion 402 within the hub 406. The latch 410 includes an actuator, such as a button, which a human user can press to resiliently deform the latch 410 to release the feature 600 of the transfer sheath 401 from the hub 406. Details of the latch 410 are described herein.

In the embodiment shown in FIGS. 4-6, 17-23 and 25, most of the proximal length of the transfer sheath 401 has a relatively constant outside diameter 602 along its length. However, a distal longitudinal portion 604 has an outside diameter 606 that is less than the outside diameter 602. In addition, a longitudinal portion 608 has an outside diameter 610 that is also less than the outside diameter 602 of most of the proximal portion of the transfer sheath 401. In some embodiments, the outside diameters 606 and 610 are equal; however, in other embodiments, the outside diameters 606 and 610 are not necessarily equal.

Although circular cross-sectional shapes are shown for the portions 604, 608 and 612, other cross-sectional shapes may be used. For example, the cross-sectional shape may be triangular or circular with two parallel face cuts, similar to two sides of a hexagonal bolt head. Optionally or alternatively, features that are proud, as opposed to recessed, for example a ridge or bump, may be used. Inside diameters of the hub 406 and/or shape of the opening in the latch 410 may be modified appropriately to facilitate insertion of the distal end portion 402 of the transfer sheath 401 into the hub 406 and/or capture of the distal end portion 402 by the latch 410.

The portions 604 and 608 are longitudinally separated from each other by another longitudinal portion 612, whose outside diameter 614 is greater than outside diameters 606 and 610. In some embodiments, the outside diameter 614 is equal to the outside diameter 602; however, in other embodiments, outside diameters 614 and 602 are not necessarily equal. The difference in diameters 606 and 614 defines a first shoulder 616. The difference in diameters 614 and 610 defines a second shoulder 618. The difference in diameters 610 and 602 defines a third shoulder 620. Although the shoulders 616-620 are shown as steps perpendicular to a longitudinal axis 622 of the transfer sheath 401, in other embodiments one or more of the shoulders 616-620 may be sloped or curved.

Figure 11:
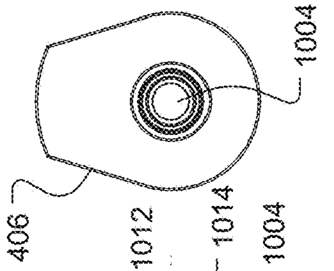
FIG. 11 is an end view of the hub of FIG. 10, according to an embodiment of the present disclosure.
Figure 13:
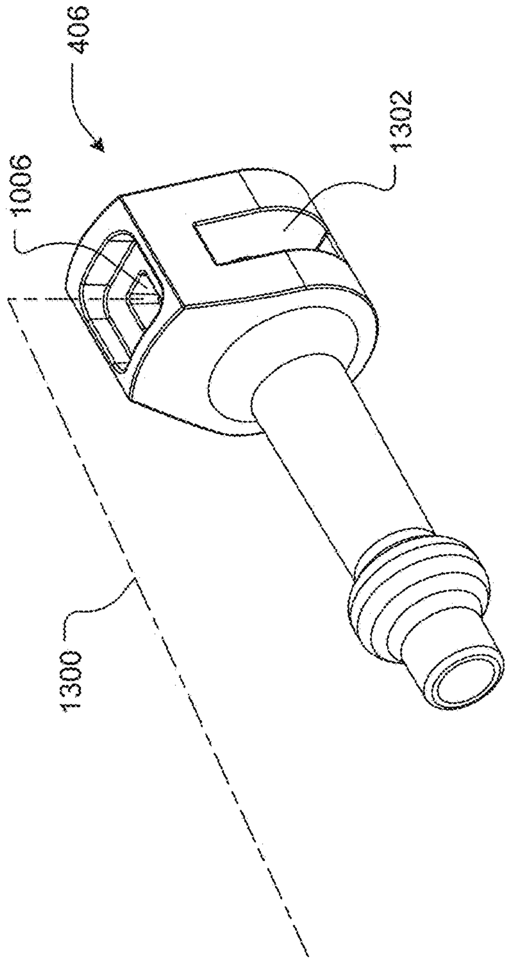
FIG. 13 is a perspective view of the hub of FIGS. 4, 5, 7, 10 and 11, according to an embodiment of the present disclosure.
Figure 12:
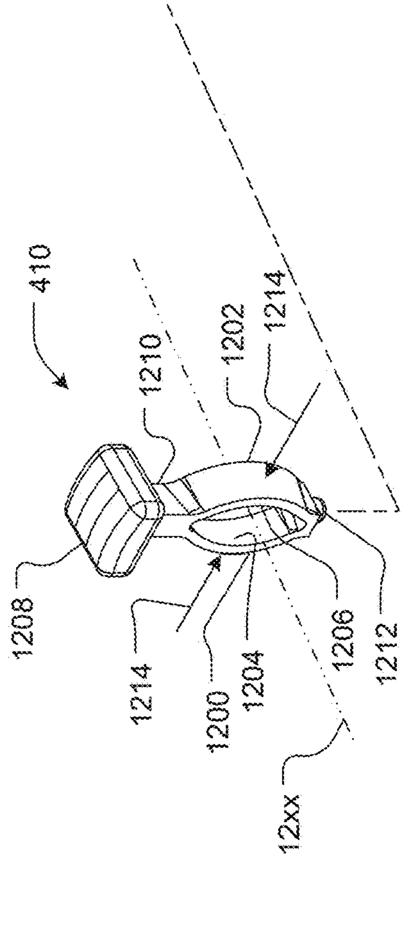
FIG. 12 is a perspective view of the latch of FIGS. 4, 5 and 7, according to an embodiment of the present disclosure.
Figure 16:
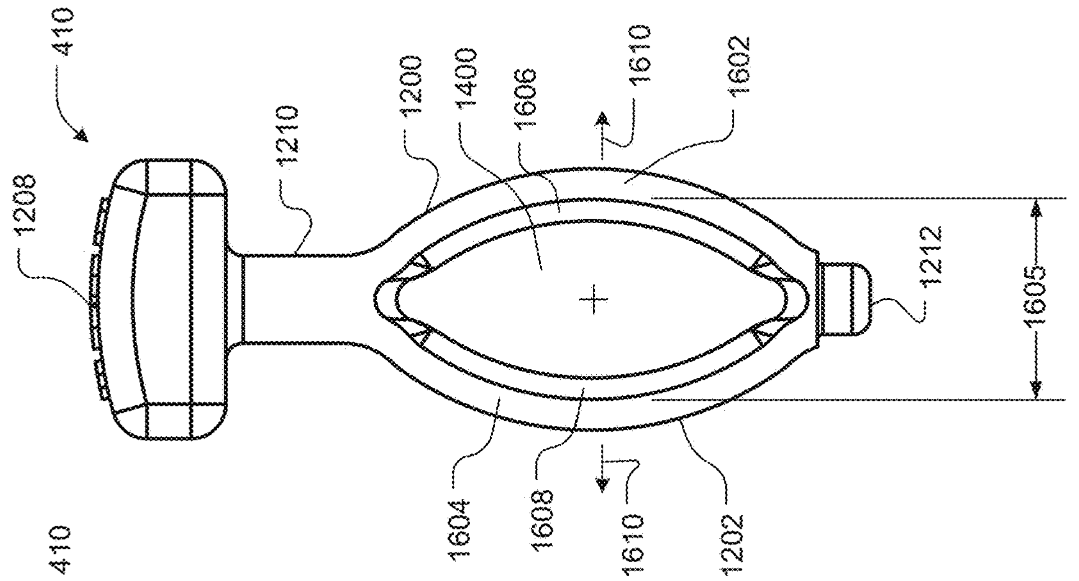
FIGS. 14-16 are respective back, cross-sectional and front views of the latch of FIGS. 4, 5, 7 and 12, according to an embodiment of the present disclosure.
Figure 15:
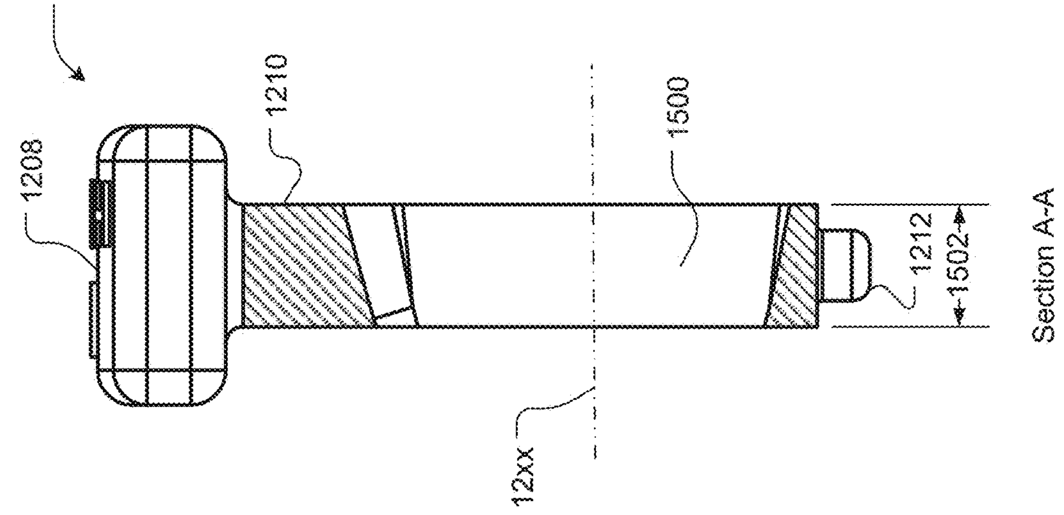
Figure 14:
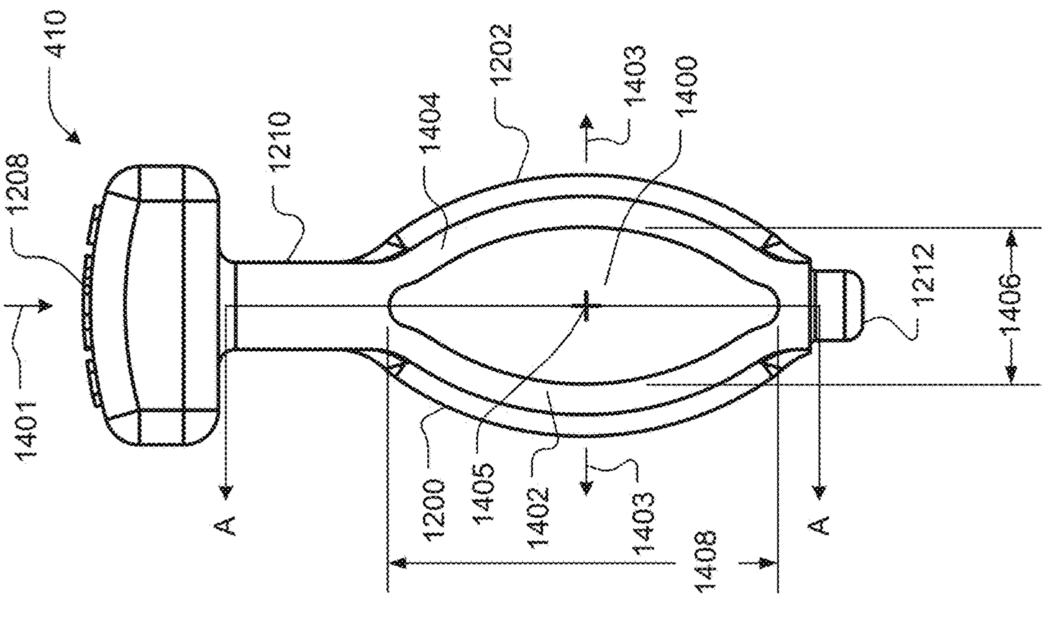

As noted, FIG. 10 is a cross-sectional view of the crimp tool 400, similar to FIG. 7, but absent the heart pump 100 and absent the latch 410. FIG. 11 is an end view of the hub 406. FIG. 12 is a perspective view of the latch 410, and FIG. 13 is a perspective view of the hub 406, absent the latch 410. FIG. 14 is a back view of the latch 410, FIG. 15 is a partial cross-sectional view of the latch 410, and FIG. 16 is a front view of the latch 410.

Figure 17:
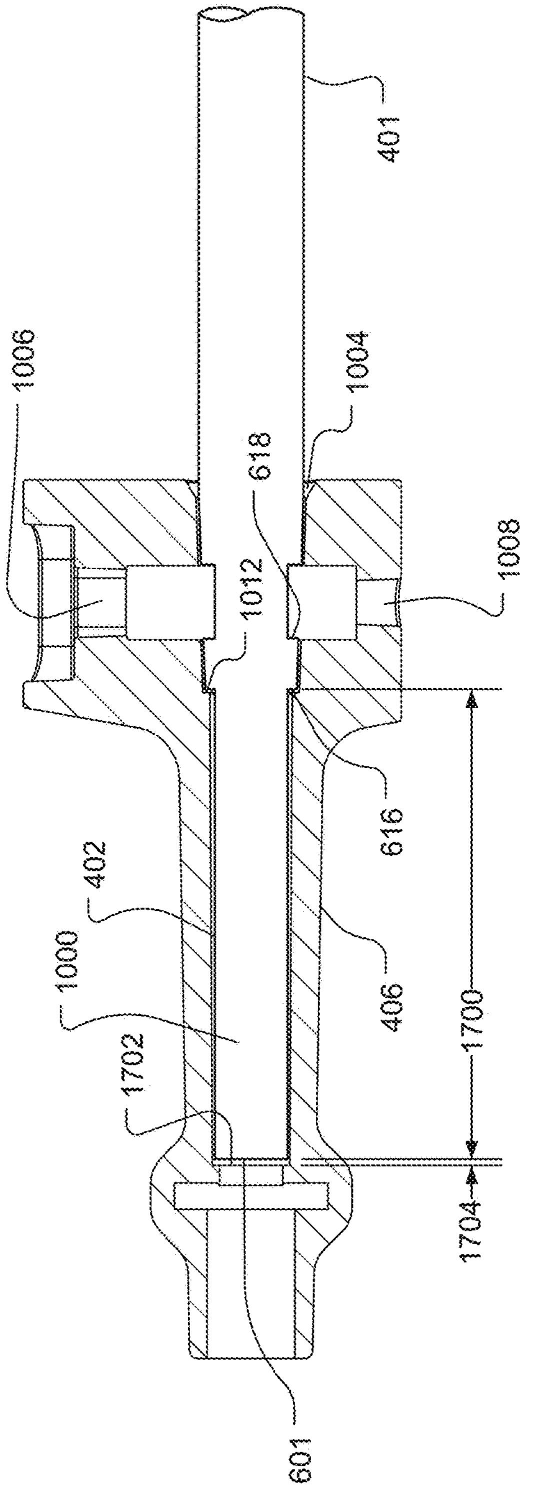
FIG. 17 is a cross-sectional view of the hub of FIGS. 4, 5, 7, 10, 11 and 13, absent the latch of FIGS. 4, 5, 7, 12 and 14-16, but with the distal end portion of the transfer sheath of FIGS. 4-6 disposed in the hub, according to an embodiment of the present disclosure.

FIG. 17 is a cross-sectional view of the hub 406, absent the latch 410, but with the distal end portion 402 of the transfer sheath 401 disposed in the hub 406. FIGS. 19-23 are perspective views of the distal end portion 402 of the transfer sheath 401 being progressively inserted into the latch 410. The hub 406 is omitted from FIGS. 19-23 for clarity.

Referring to FIG. 12, the latch 410 includes two resilient arcuate pillars (first and second pillars) 1200 and 1202. Respective concave sides 1204 and 1206 of the arcuate shapes counterface each other. An actuator 1208 is mechanically coupled to the first and second pillars 1200 and 1202 by a neck 1210. Optionally, the latch 410 includes a locating pin 1212, on an opposite side of the first and second pillars 1200 and 1202 from the actuator 1208.

Figure 18:
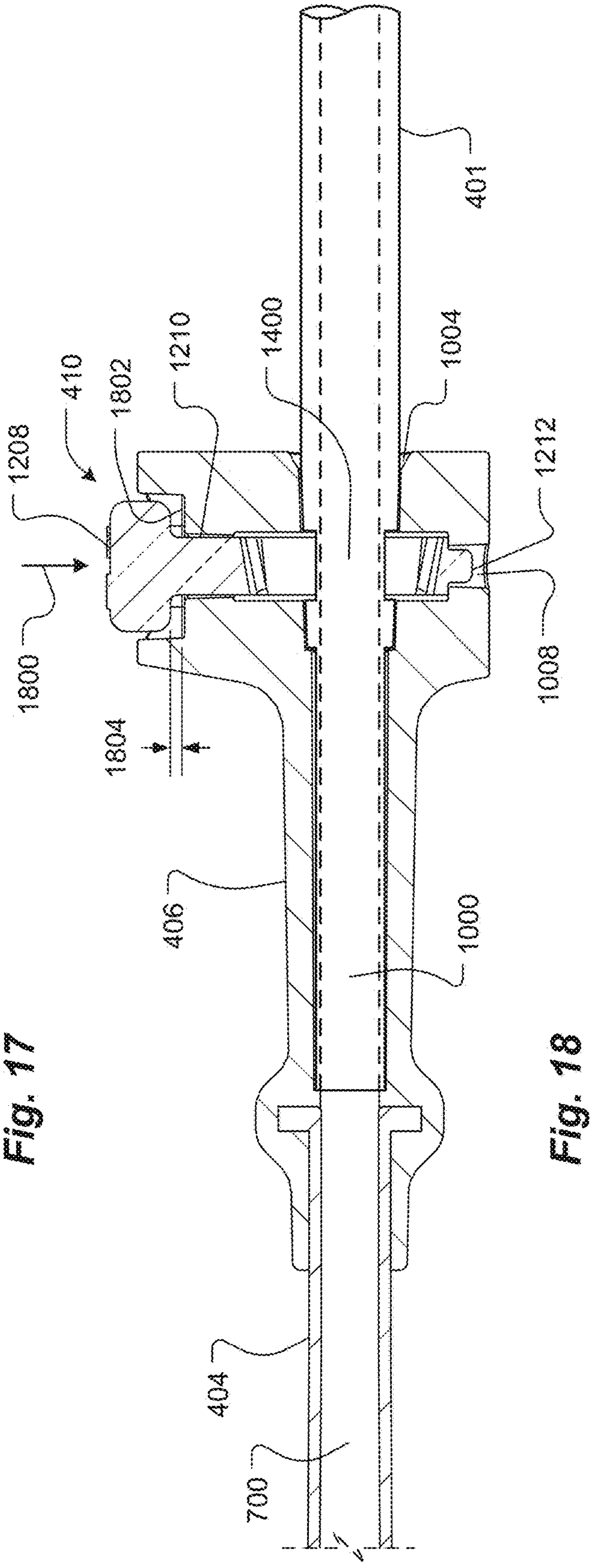
FIG. 18 is a cross-sectional view of the hub of FIGS. 4, 5, 7, 10, 11, 13 and 17 and the latch of FIGS. 4, 5, 7, 12 and 14-16, with the latch installed in the hub, according to an embodiment of the present disclosure.
Figure 19:
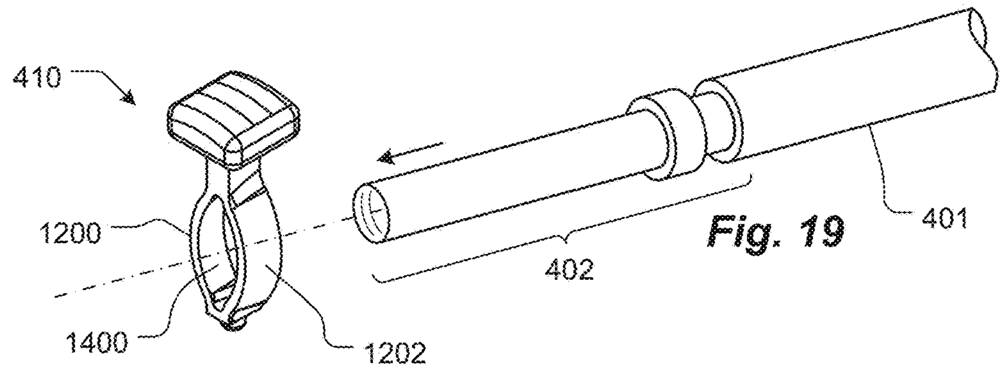
FIGS. 19-23 are perspective views of the distal end portion of the transfer sheath of FIGS. 4-6 being progressively inserted into the latch of FIGS. 4, 5, 7, 12 and 14-16, with the hub of FIGS. 4, 5, 7, 10, 11, 13, 17 and 18 omitted for clarity, according to an embodiment of the present disclosure.
Figure 20:
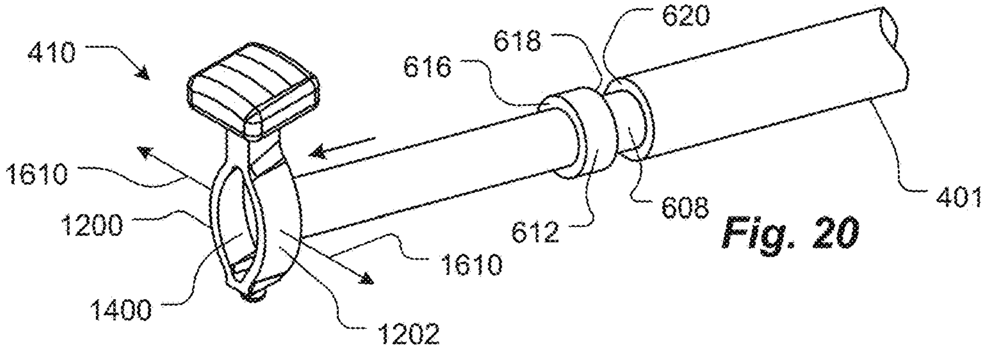
Figure 21:
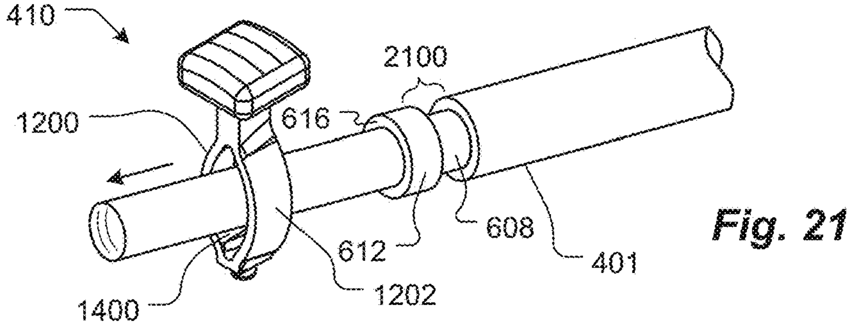

Alternating long-short dashed line 1300 (extending between FIGS. 12 and 13) indicates how the latch 410 fits into the hub 406. The two pillars 1200 and 1202 are resiliently squeezed toward each other, as indicated by arrows 1214, to temporarily narrow a space between the pillars 1200 and 1202, so the two pillars 1200 and 1202 fit through an aperture 1006 (FIGS. 10 and 13) defined by the hub 406. The locating pin 1212 fits into an opening 1008 (FIG. 10) in the bottom of the hub 406. Alternatively, the hub 406 includes an upward directed locating pin, and the latch 410 defines an opening. Once disposed within the hub 406, the two pillars 1200 and 1202 rebound, at least partially, toward their original shapes and enter respective voids, exemplified by void 1302, defined by the hub 406 to prevent the latch 410 inadvertently dislodging from the hub 406. FIG. 18 is a cross-sectional view of the hub 406 and the latch 410, with the latch 410 installed in the hub 406.

As noted, FIGS. 14 and 16 are respective back and fronts views of the latch 410. The first and second pillars 1200 and 1202 collectively define an elongated opening 1400 therebetween. As noted, the first and second pillars 1200-1202 are resilient. Therefore, if a force is applied vertically on the pillars 1200-1202, as indicated by an arrow 1401, while the bottoms of the pillars 1200-1202 (proximate the locating pin 1212) are restrained, the pillars 1200-1202 deform outward, as indicated by arrows 1403. In addition, a center 1405 of the opening 1400 moves down slightly. However, for purposes of this disclosure and the claims, this vertical movement of the center 1405 is ignored and the center 1405 is assumed to remain fixed, relative to the latch 410. As can be seen in FIG. 18, the hub bore 1000 extends through the opening 1400, coaxially with the tube bore 700.

Referring again to FIG. 14, each pillar 1200 and 1202 has a respective back surface 1402 or 1404, and referring to FIG. 16, each pillar 1200 and 1202 has a respective front surface 1602 or 1604. The opening 1400 extends from the front surfaces 1602-1604 to the back surfaces 1402-1404 to define a passage 1500 (FIG. 15). The passage 1500 is tapered to be narrower at the back surfaces 1402-1404 than at the front surfaces 1602-1604. Width of the opening 1400 at the back surfaces 1402-1404 is indicated at 1406, and width of the opening 1400 at the front surfaces 1602-1604 is indicated at 1605. This taper is evident from side walls 1606 and 1608 of the passage 1500 being visible in the front view of FIG. 16, but not in the back view of FIG. 14.

Due to this taper, as the distal end portion 402 of the transfer sheath 401 is inserted into the opening 1400 at the front surfaces 1200-1202 (FIG. 19), in some embodiments the distal end portion 402 spreads apart the two pillars 1200 and 1202, as indicated by arrows 1610 (FIGS. 16 and 20), distorting the pillars 1200 and 1202. The pillars 1200 and 1202 are configured to resiliently displace away from each other, in response to insertion of the distal end portion 402 of the transfer sheath 401.

As the distal end portion 402 of the transfer sheath 401 is further advanced (FIG. 21) through the opening 1400, the side walls 1606 and 1608 bear against the outside wall of the transfer sheath 401, due to the resilience and deformation of the pillars 1200 and 1202.

Figure 22:
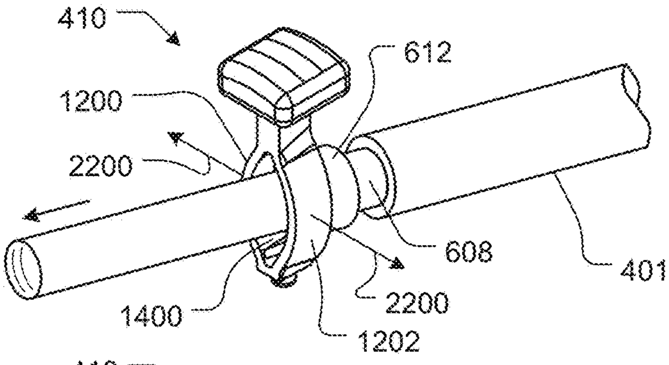

As shown in FIG. 22, when the portion 612 of the transfer sheath 401 enters the opening 1400, the portion 612 further resiliently separates the pillars 1200 and 1202, as indicated by arrows 2200. That is, the first shoulder 616 (FIG. 6) spreads apart the pillars 1200 and 1202. In some embodiments, the distal end portion 402 of the transfer sheath 401 is insufficiently large in outside diameter to displace the pillars 1200 and 1202 away from each other. Instead, the pillars 1200 and 1202 are first displaced away from each other by the first shoulder 616.

Figure 23:
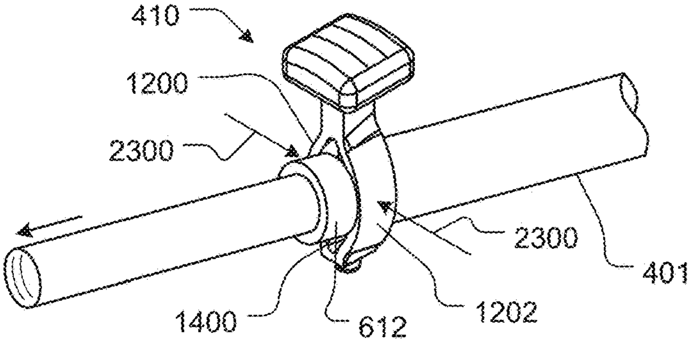

As shown in FIG. 23, once the portion 612 of the transfer sheath 401 exits the opening 1400, the pillars 1200 and 1202 rebound, as indicated by arrows 2300, to bear on the outside diameter 610 of the portion 608 of the transfer sheath 401. The portion 608 is longitudinally long enough to accept width 1502 (FIG. 15) of the pillars 1200 and 1202. The second shoulder 618 (FIGS. 6 and 20) defined at changes in outside diameters 610 and 614 of portions of the transfer sheath 401 limit or prevent longitudinal travel of the transfer sheath 401, once the pillars 1200 and 1202 have dropped into a notch 2100 (FIG. 21) defined between the shoulders 2000 and 2002. Optionally, the third shoulder 620 also limits or prevents longitudinal travel of the transfer sheath 401, once the pillars 1200 and 1202 have dropped into the notch 2100. The second shoulder 618 defines the mechanical feature 600 that may be engaged by the latch 410 to releasably restrain the distal end portion 402 of the transfer sheath 401 in the hub 406. Optionally, the mechanical feature 600 also includes the notch 2100 and/or the third shoulder 620, to prevent or limit longitudinal travel of the transfer sheath 401 further into the hub 406, once the pillars 1200 and 1202 have dropped into the notch 2100.

Hub (Continued)

As noted, FIG. 10 is a cross-sectional view of the crimp tool 400, absent the heart pump 100 and absent the latch 410. Inside diameters (collectively an internal profile 1010) of the hub 406 should match outside diameters 606, 614, 610 and 602 (FIG. 6) of the distal end portion 402 of the transfer sheath 401, allowing sufficient space between the inside walls of the hub 406 and the outside walls of the distal end portion 402 for at least a clearance fit, taking into account expected manufacturing tolerances.

The hub 406 defines a shoulder 1012 in the hub bore 1000, which acts as a stop to limit how far the transfer sheath 401 can be inserted into the hub bore 1000. FIG. 17 is a cross-sectional view of the hub 406, absent the latch 410, but with the distal end portion 402 of the transfer sheath 401 disposed in the hub 406. The shoulder 1012 limits how far the first shoulder 616 of the distal end portion 402 of the transfer sheath 401 can be inserted into the hub 406. Position of the shoulder 1012 and length 1700 of the distal longitudinal portion 604 of the transfer sheath 401 should be selected such that, when the transfer sheath 401 is fully inserted into the hub bore 1000, that is, the first shoulder 616 abuts the stop 1012, the extreme distal end portion 601 of the transfer sheath 401 dose not reach a shoulder 1702 defined in the hub bore 1000, but instead the extreme distal end portion 601 is spaced a small distance 1704 from the shoulder 1702. The space 1704 prevents damaging the extreme distal end portion 601 of the transfer sheath 401.

Thus, restraining the distal end portion 402 of the transfer sheath 401 in the hub 406 simply involves inserting the distal end portion 402 into the hub bore 1000, until the first shoulder 616 contacts the stop 1012. At that insertion distance, the pillars 1200 and 1202 rebound, as discussed with respect to FIG. 23, and the shoulder 618 (FIG. 20) prevents longitudinal withdrawal of the transfer sheath 401.

To release the distal end portion 402 from the hub 406, a user presses the actuator 1208. The actuator 1208 is configured for activation by a human. When fitted into the hub 406, the actuator 1208 presents a push button (visible, for example, in FIGS. 5 and 18) that can be pressed by the human user in a direction indicated by an arrow 1800 (FIG. 18). The neck 1210 of the latch 410 is sufficiently long to make the actuator 1208 stand proud of a shoulder 1802 defined by the hub 406 by a distance 1804. The shoulder 1802 limits downward 1800 travel of the actuator 1208.

Figure 24:
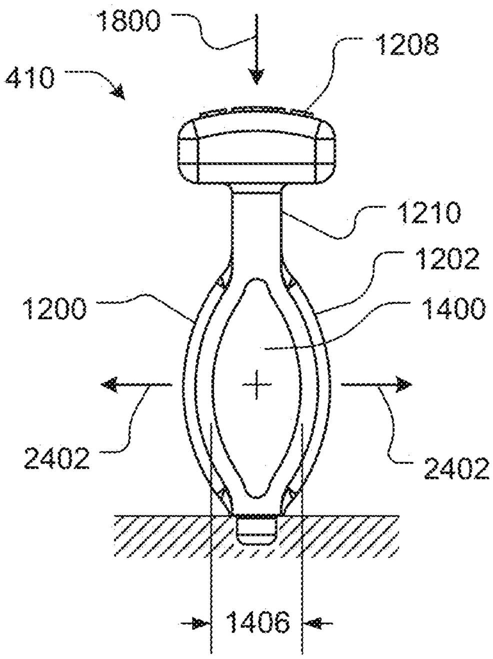
FIG. 24 is a back view of the latch of FIGS. 4, 5, 7, 12 and 14-16, similar to FIG. 14, according to an embodiment of the present disclosure.
Figure 25:
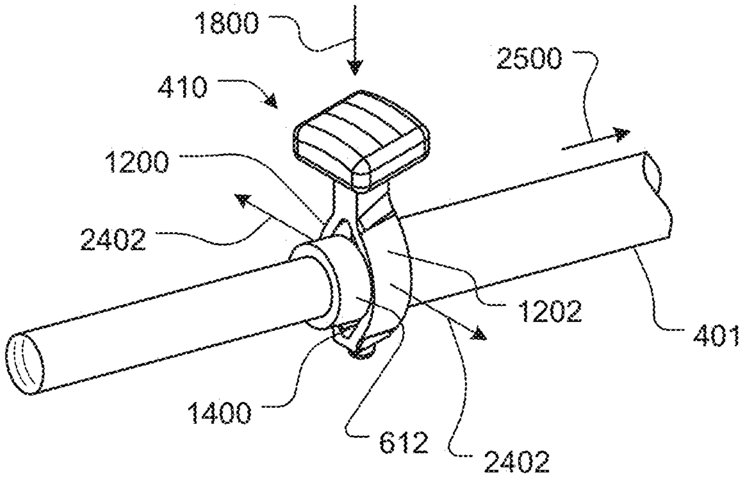
FIG. 25 is a perspective view of the distal end portion of the transfer sheath of FIGS. 4-6 being removed from the latch of FIGS. 4, 5, 7, 12 and 14-16, with the hub of FIGS. 4, 5, 7, 10, 11, 13, 17 and 18 omitted for clarity, according to an embodiment of the present disclosure.

As illustrated in FIGS. 24 and 25, pressing down 1800 on the actuator 1208, while the bottoms of the pillars 1200 and 1202 are restrained, causes the pillars 1202 and 1204 to bend outward, as indicated by arrows 2402, thereby increasing the width 1406 of the opening 1400. The distance 1804 (FIG. 18) and geometry and material of the pillars 1202 and 1204 are chosen such that pressing the actuator 1208 no more than the distance 1804 cause the opening 1400 to widen to at least the outside diameter 614 (FIG. 6) of the portion 612 of the distal end portion 402. Consequently, the portion 612 clears the side walls 1606 and 1608 (FIG. 16) of the passage 1500, and the distal end portion 402 may be withdrawn from the hub 406, as indicated by arrow 2500.

The opening 1400 is eccentric, as viewed along a longitudinal axis 1014 (FIG. 10) of the tube 404, although the opening 1400 need not be elliptical. "Eccentric" herein means how much a shape deviates from circular. Eccentricity may be taken as a ratio of major axis dimension 1408 (FIG. 14) to minor axis dimension 1406 or 1605 (FIGS. 14 and 16). Essentially, the pillars 1200 and 1202 form an eccentric radial spring, and the eccentricity of the radial spring can be decreased by pressing on the actuator 1208.

The actuator 1208 can be either pressed down or not pressed down. Thus, the actuator 1208 can be thought of as having an activated mode and an inactivated mode, where pressing down the actuator 1208 puts the actuator in the activated mode, and not pressing or releasing the actuator 1208 puts the actuator in the inactivated mode.

As noted, pressing the actuator 1208 causes the pillars 1200 and 1202 to bend. Thus, each of the two pillars 1200 and 1202 can be bent outward, as indicated by arrows 2402, to increase the width 1406 of the opening 1400 to release the distal end portion 402 of the transfer sheath 401 from the hub 406, or the pillars 1200 and 1202 can be in their respective unbent shapes. Thus, each pillar 1200 and 1202 can be thought of as having an activated mode and an inactivated mode, where having been bent as a result of the actuator 1208 being pressed puts the pillars 1200 and 1202 in the activated mode, and rebounding or not having been bent puts the pillars 1200 and 1202 in the inactivated mode.

Each pillar 1200 and 1202 is mechanically coupled to the actuator 1208 and is configured to resiliently transition from the inactivated mode to the activated mode in response to activation of the actuator 1208. As noted, the pillars 1200 and 1202 collectively define an opening 1400 therebetween. In the inactivated mode of the pillars 1200 and 1202, a smallest dimension 1406 (FIG. 14) of the opening 1400, as viewed along the longitudinal axis 1014 (FIG. 10) of the tube 404, is smaller than in the activated mode of the pillars 1200 and 1202.

As noted, inserting the distal end portion 402 of the transfer sheath 401, or the first shoulder 616, into the hub 406 increases the width 1406 of the opening 1400. This increase in the width 1406 does not require that the actuator 1208 be pressed. Thus, the pillars 1200 and 1202 are configured to resiliently displace away from each other, independently of activation of the actuator 1208.

Although a latch 410 with symmetric pillars 1200 and 1202 has been described, in other embodiments the pillars need not necessarily be symmetric. For example the pillars may be skew to each other. A first pillar may be arcuate shaped, and another pillar may be straight or have another shape, different from the first pillar. Some embodiments have more or fewer than two pillars.

Peel-Away Sheath

Figure 26:
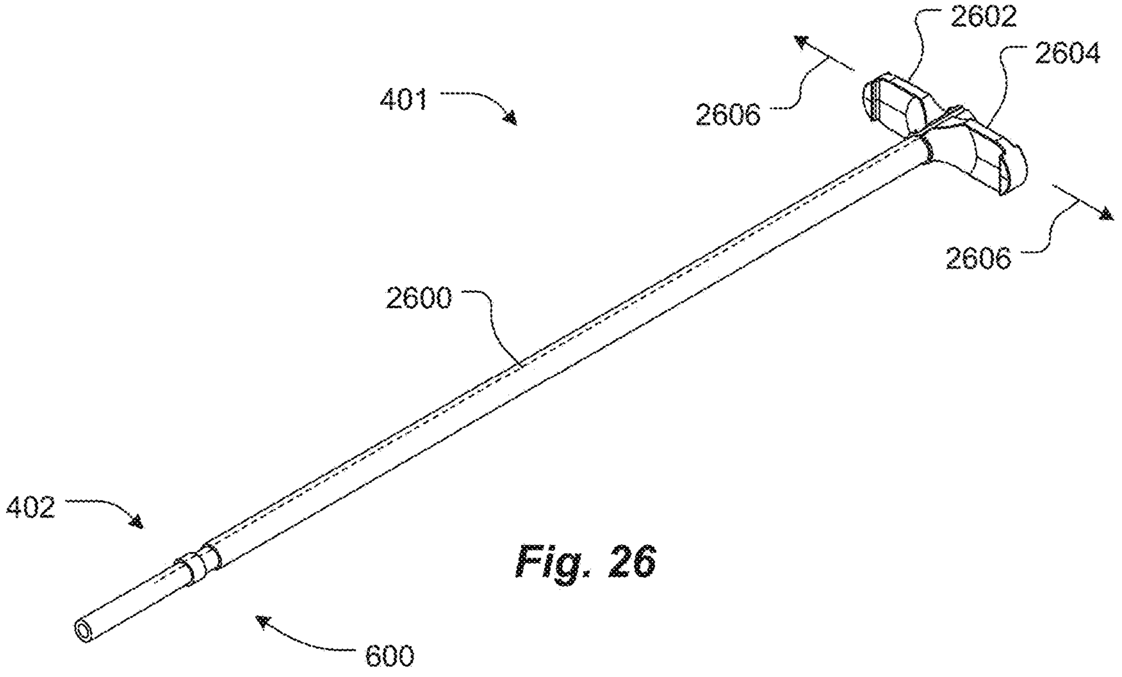
FIG. 26 is a perspective view of a peel-away sheath that may be used as the tubular transfer sheath of FIGS. 4-7, 17-23 and 25, according to an embodiment of the present disclosure.

In some embodiments, as shown in FIG. 26, the tubular sheath 401 defines one, two or more parallel longitudinal regions, exemplified by region 2600, that weaken the tubular sheath 401, to facilitate peeling apart the tubular sheath 401, once the compressed heart pump 100 has been removed from the tubular sheath 401. Each region 2600 may, for example, define a groove to reduce wall thickness of the tubular sheath 401, to facilitate a predetermined and controlled failure in the wall, when ears 2602 and 2604 are pulled apart, as indicated by arrows 2606. In other respects, the tubular sheath 401 of FIG. 26 is similar to the tubular sheath 401 described elsewhere in this disclosure, and descriptions of the tubular sheath 401 apply, mutatis mutandis, to the tubular sheath of FIG. 26. For example, the mechanical feature 600 of the tubular sheath 401 may be engaged by the latch 410, or an alternative latch, to releasably restrain the distal end portion 402 in the hub 406, as described herein.

Alternative Latches

As noted, the latch 410 has two resilient arcuate pillars 1200 and 1202, such that a force applied vertically on the pillars 1200-1202, as indicated by the arrow 1401 (FIG. 4), causes the pillars 1200-1202 to deform outward, as indicated by arrows 1403, thereby increasing the width 1406 of the opening 1400, to release the mechanical feature 600 of the tubular sheath 401. However, alternative latches are contemplated.

Figure 29:
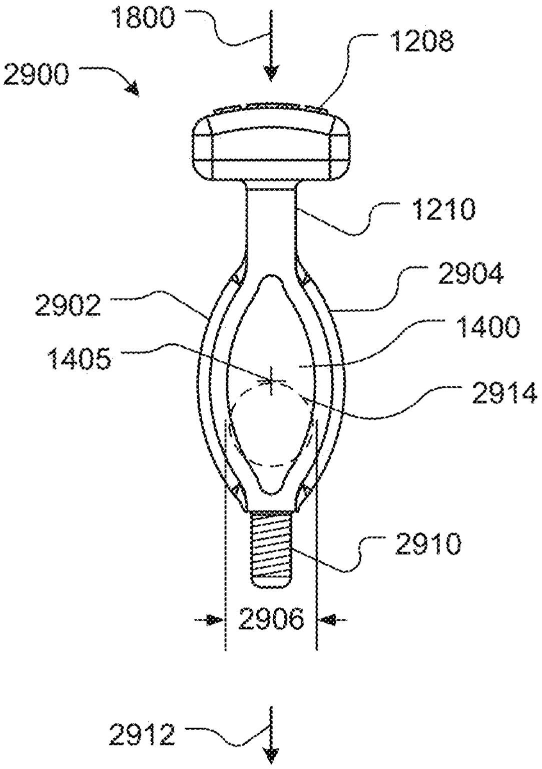
FIG. 29 is a back view of a latch, according to another embodiment of the present disclosure.

A first alternative latch 2900 is shown in FIG. 29. In this embodiment, pillars 2902 and 2904 do not material deform, and the width 2906 of the elongated opening 1400 does not materially change, when the latch 2900 is activated, i.e., when the force 1800 is applied vertically down on the actuator 1208. Instead, a spring 2910 compresses vertically, so the opening 1400 translates downward, along an elongation axis of the opening 1400, as indicated by an arrow 2912. In this embodiment, the width 2906 of the opening 1400 is sufficient for the portion 612 of the distal end portion 402 to pass through the opening 1400, without materially outwardly deforming the pillars 2902-2904. That is, the width 2906 is at least equal to the diameter 614 (FIG. 6).

The center 1405 of the opening 1400 is above the longitudinal axis of the hub bore 1000 and the tapered tube bore 700. Approximate relative position of the hub bore 1000 and the tube bore 700 are indicated by a dashed circle 2914. Inserting the distal end portion 402 of the transfer sheath 401 into the latch 2900 causes the pillars 2902-2904 to translate downward, due to the taper of the passage 1500, from the front surfaces (corresponding to front surfaces 1602-1604 of the latch 410) to the back surfaces (corresponding to back surfaces 1402-1404 of the latch 410) of the pillars 2902-2904. This downward translation compresses the spring 2910. However, once the portion 612 of the transfer sheath 401 has translated through the opening 1400, the spring 2910 rebounds, the elongated opening 1400 translates upward, and the latch 2900 captures the mechanical feature 600.

The latch 2900 can be released by depressing the actuator 1208 to once again lower the opening 1400 and release the mechanical feature 600. In other respects, the latch 2900 is similar to the latch 410, and descriptions of the latch 410 apply, mutatis mutandis, to the latch 2900.

Figure 30:
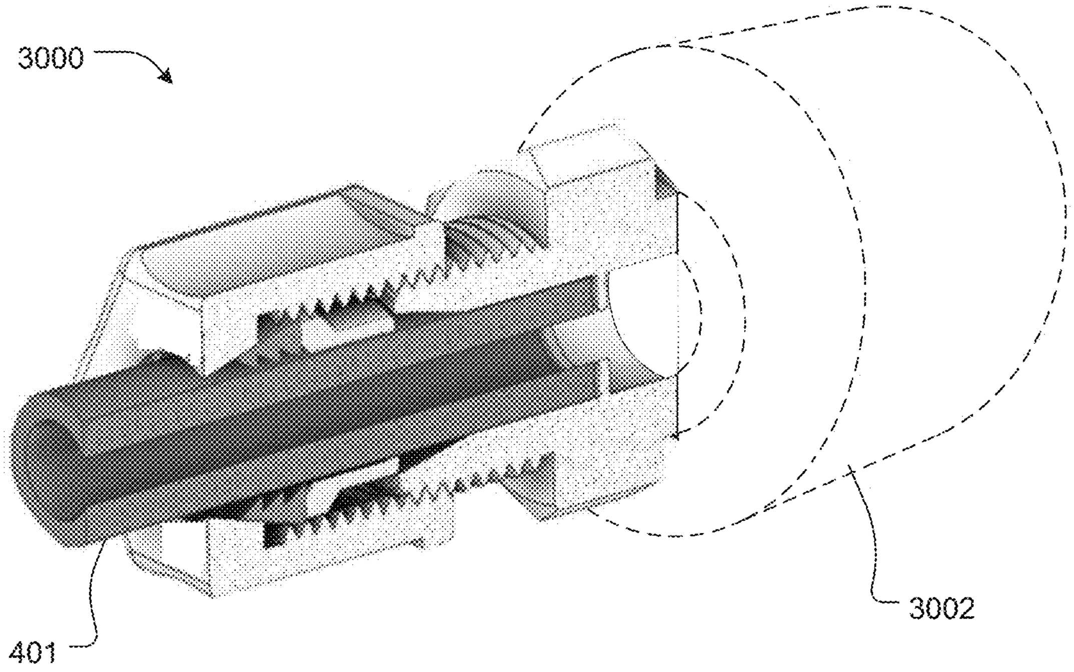
FIG. 30 is a perspective, partial cross-sectional, view of a latch, according to yet another embodiment of the present disclosure.

A second alternative latch 3000 is shown in FIG. 30. The second alternative latch 3000 includes a threaded compression fitting that clamps around the distal end portion 402 of the tubular sheath 401. In this case, the distal end portion 402 need not necessarily define a mechanical feature 600. The distal end portion 402 may be of constant outside diameter. Remainder of the hub 406 is shown in dashed line 3002.

Figure 31:
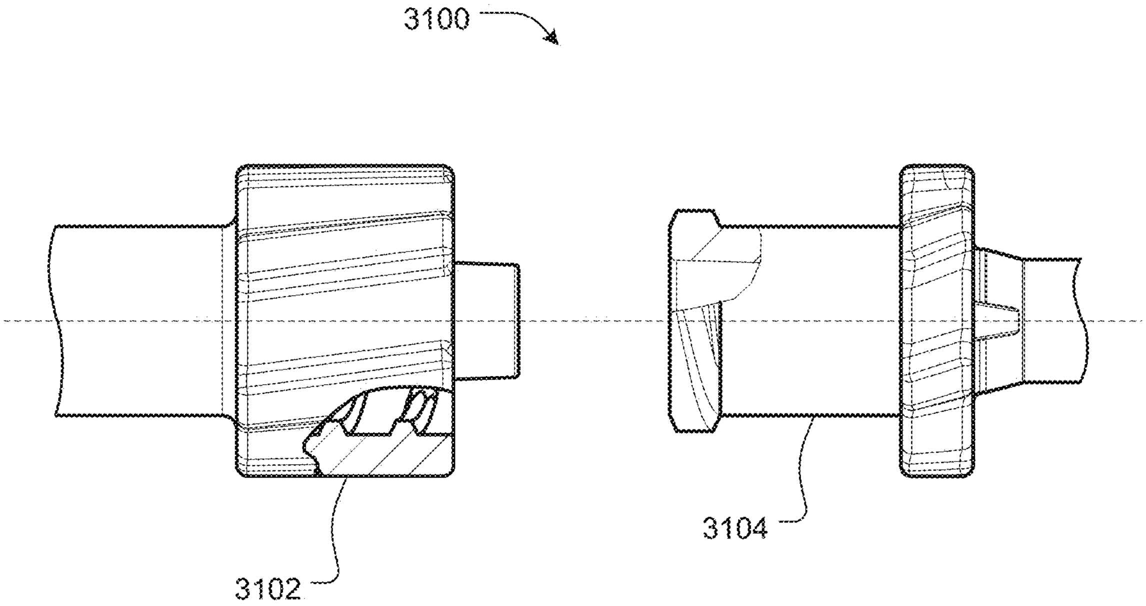
FIG. 31 is a side, partial cross-sectional, view of a latch, according to a third alternative embodiment of the present disclosure.

A third alternative latch 3100 is shown in FIG. 31. The third alternative latch 3100 includes complementary male and female threaded connectors 3102 and 3104, such as Luer connectors. One of the two threaded connectors 3102 or 3104 is connected to, or part of, the hub 406, and the other of the two threaded connectors 3102 or 3104 is connected to, or part of, the distal end portion 402 of the tubular sheath 401. In this embodiment, the tubular sheath 401 is detachably attached to the hub 401 by mating the complementary male and female threaded connectors 3102 and 3104.

Other latch mechanisms, such as ball detents, snap locks or locking pins, are also contemplated.

Introducer

Figure 27:
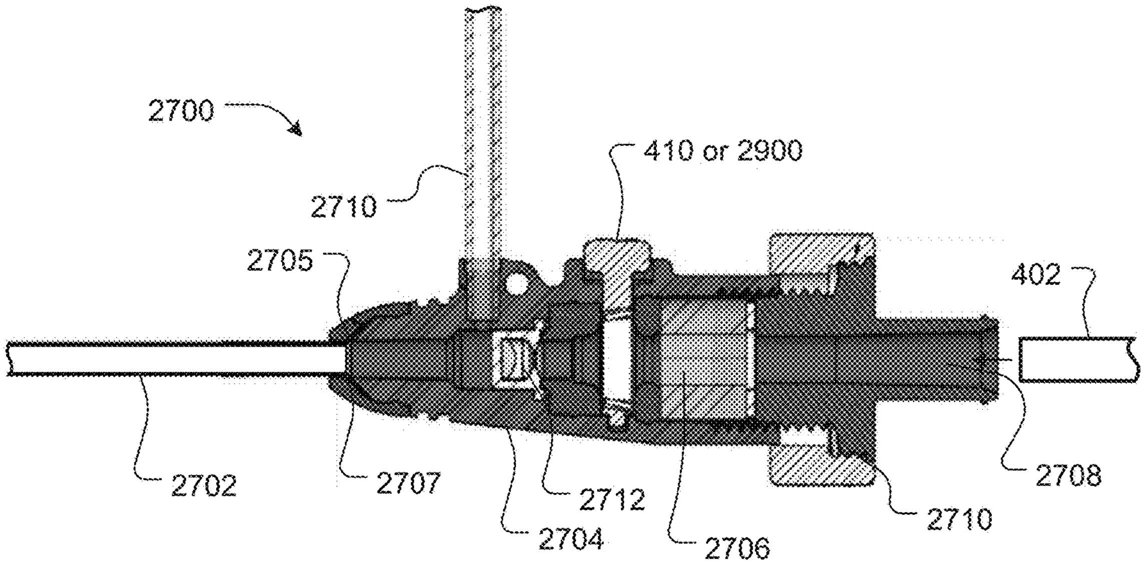
FIG. 27 is a cross-sectional view of a portion of an introducer, to which the tubular transfer sheath of FIGS. 4-7, 17-23 and 25 or 26 may be coupled, according to an embodiment of the present disclosure.

FIG. 27 is a cross-sectional view of a portion of an introducer 2700, according to an embodiment of the present disclosure. The introducer 2700 includes an introducer sheath 2702 and a hub 2704. A dilator (not shown) may be used with the introducer 2700. The hub 2704 defines a hub bore 2706 coaxial with the introducer sheath 2702. One end 2705 of the hub bore 2706 is coupled to a proximal end 2707 of the introducer sheath 2702. The other end 2708 of the hub bore 2706 is configured to receive the distal end portion 402 of the transfer sheath 401 approximately coaxially with the introducer sheath 2702, similar to the way the hub 406 of the crimp tool 400 is configured to receive the distal end portion 402 of the transfer sheath 401.

Optionally, in some embodiments, the hub 2704 includes a latch 410 or 2900, as described herein with respect to FIGS. 4, 5, 7, 12-16 and 18-25 or 29, to releasably restrain the distal end portion 402 of the tubular sheath 401, as described herein. In some embodiments, the introducer hub 2704 includes one or more Tuohy-Borst adapters, exemplified by Tuohy-Borst valve 2710, to releasably tighten around a circumference of the introducer sheath 2702 and/or the distal end portion 402 of the transfer sheath 401 to releasably hold the sheath or distal end portion in place and provide a fluid-tight seal. Essentially, such a valve 2710 provides a threaded compression fitting latch. Alternatively, the hub 2704 includes a latch 3100, as described herein. Optionally, the introducer hub 2704 defines a purge port 2710. For example, the introducer hub 2704 may include a combination ring and slit valve 2712. The slit valve portion seals when no catheter 110 and/or sheath 402 is in the introducer hub 2704, and the ring valve seals when the distal end portion 402 of the transfer sheath 401, catheter 110, or a dilator is in place.

The introducer hub 2704 may include one or more valves, as needed, to maintain hemostasis. In other respects, the introducer hub 2704 of FIG. 27 is similar to the hub 406 described elsewhere in this disclosure, and those descriptions apply, mutatis mutandis, to the hub 2704. For example, hub bore 2706 may define an internal profile similar to the internal profile 1010 described with respect to FIG. 10. Alternatively or additionally, the internal profile may be formed together with one or more valves and/or respective valve retainers.

Frangible Crimp Tool

Figure 28:
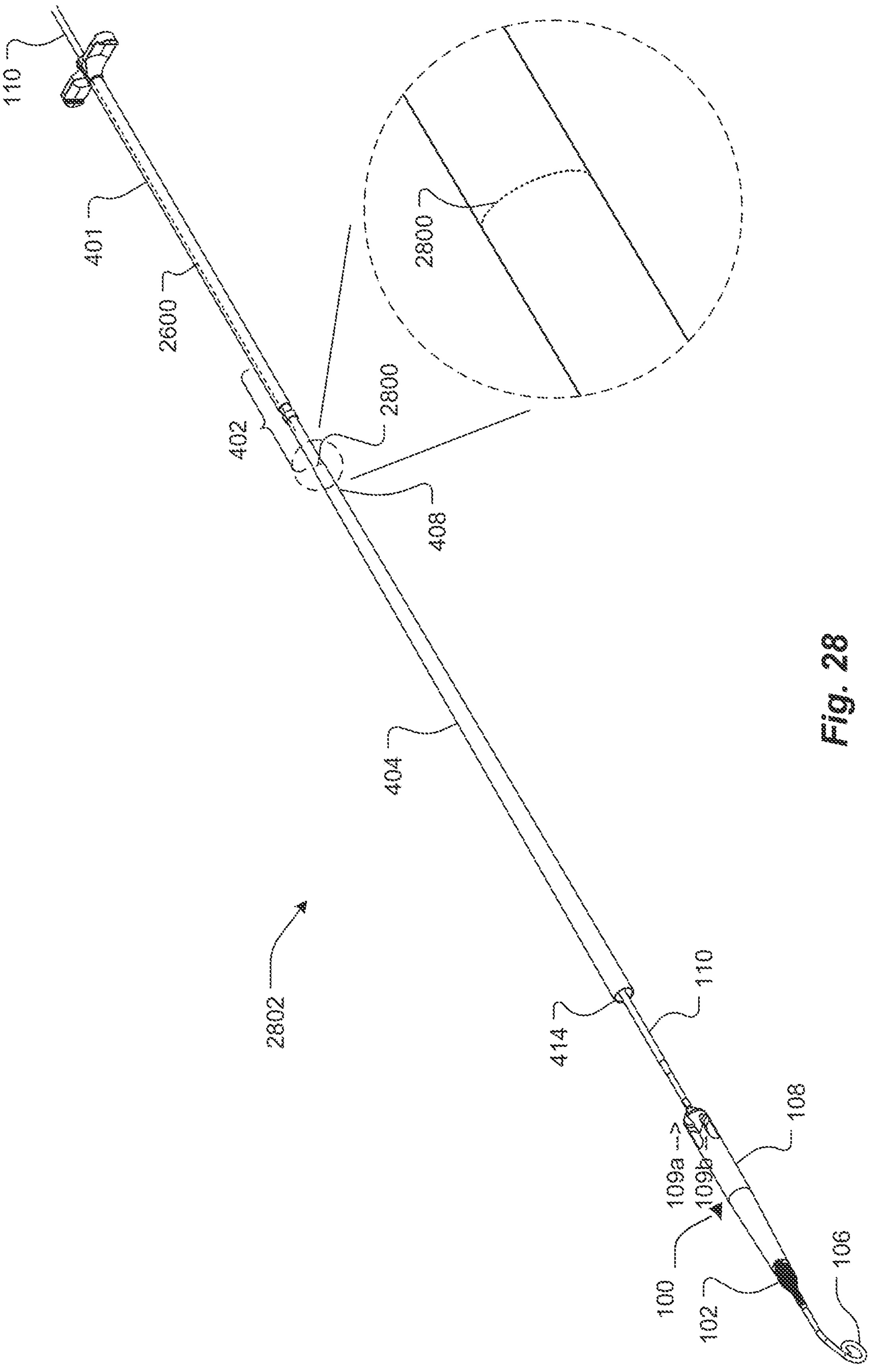
FIG. 28 is a perspective view of a frangible crimp tool for crimping a resiliently radially compressible human-implantable catheter pump, such as the heart pump of FIGS. 1-2, and transferring the crimped pump into a tubular transfer sheath, which initially is part of the frangible crimp tool, according to another embodiment of the present disclosure.

As noted, and as shown in FIG. 28, in some embodiments, the distal end portion 402 of the tubular sheath 401 is detachably attached to the proximal end 408 of the tapered tube 404, such as by a frangible portion 2800, without necessarily including a hub between the tapered tube 404 and the tubular sheath 401. The distal end portion 402 of the tubular sheath 401 is coaxially coupled to the proximal end 408 of the tapered tube 404 by the frangible portion 2800. In these embodiments, once the crimped pump is pulled by the catheter 110 into the tubular sheath 401, the frangible portion 2800 is broken to free the tubular sheath 401 from the tapered tube 404. Before the frangible portion 2800 is broken, the tapered tube 404 and the tubular sheath 401 are collectively referred to as a crimp tool 2802. Optionally, as discussed with respect to FIG. 26, the tubular sheath 401 defines one, two or more parallel longitudinal regions, exemplified by region 2600, that weaken the tubular sheath 401, to facilitate peeling apart the tubular sheath 401, once the compressed heart pump 100 has been removed from the tubular sheath 401. In other respects, the tapered tube 404 and the tubular sheath 401 of the crimp tool 2802 are similar to those described elsewhere herein.

Methods

Figure 32:
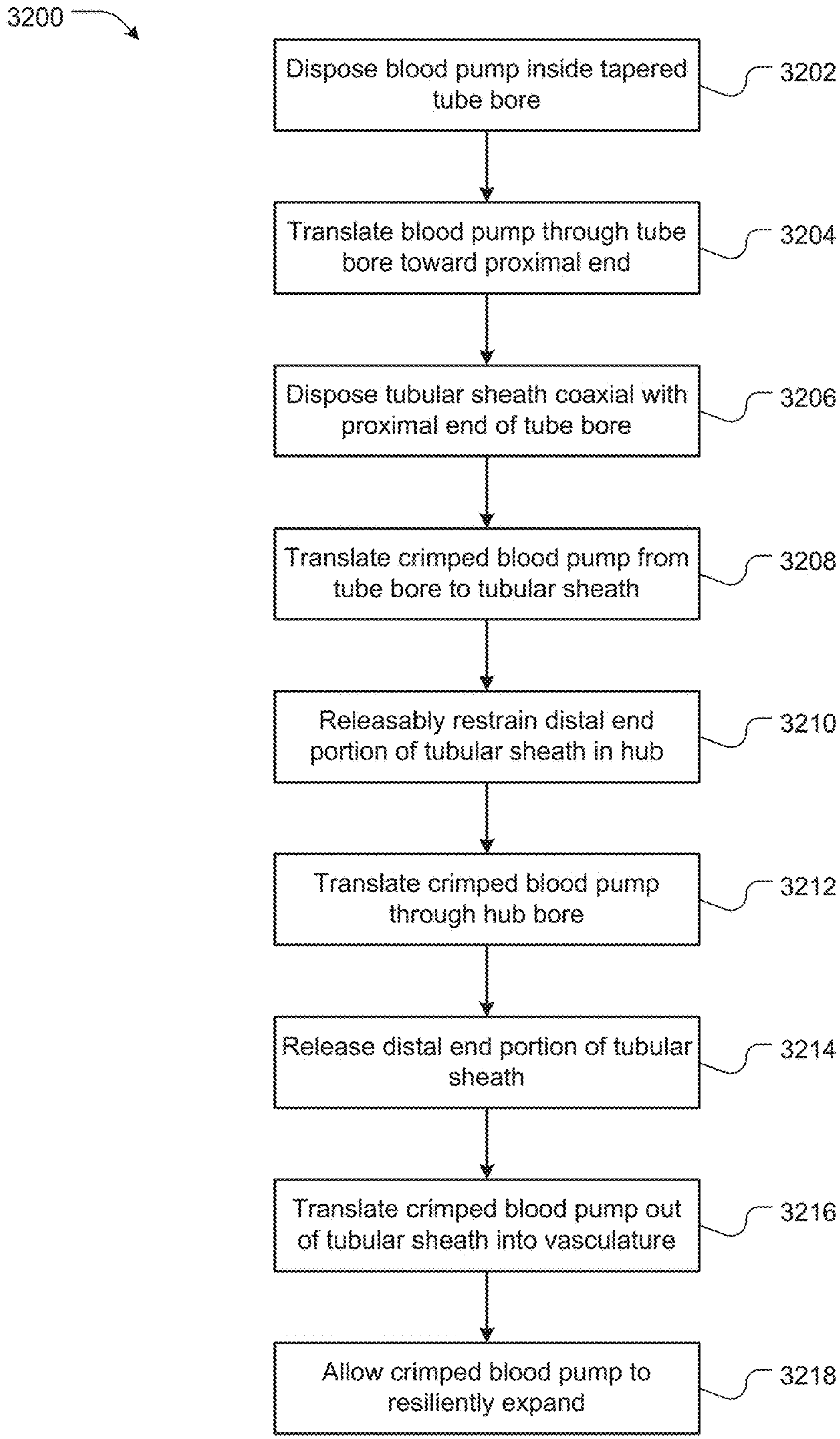
FIGS. 32 and 33 are flowcharts that schematically illustrates methods for crimping a blood pump, according to respective embodiments of the present disclosure.

FIG. 32 is a flowchart that schematically illustrates a method 3200 for crimping a blood pump. The method 3200 may, for example, be practiced using the crimp tool 400 described herein. The method includes disposing 3202 the blood pump inside a distal end of a tapered longitudinal tube bore. The tube bore is defined by an elongated tube. The tube bore is at least about 30 mm long. The tube bore has an inside dimension that tapers along the length of the tube bore from (a) at least about a maximum outside dimension of the pump at the distal end of the tube bore to (b) at most about 4 mm in diameter at a proximal end of the tube bore.

At 3204, the blood pump is translated through the tube bore in a direction toward the proximal end of the tube bore, including contacting an outside surface of the blood pump with an inside surface of the elongated tube as the blood pump translates through the tube bore, thereby crimping the blood pump to produce a crimped blood pump.

In some embodiments, translating the blood pump includes pulling the blood pump through the tube bore. However, in principle, translating the blood pump can involve pushing the blood pump through the tube bore.

In some embodiments, the inside dimension of the distal end of the tube bore is at least about 7 mm. In some embodiments, the inside dimension of the proximal end of the tube bore is at most about 4 mm. In some embodiments, the inside dimension of the distal end of the tube bore is at least about 7 mm, and the inside dimension of the proximal end of the tube bore is at most about 4 mm. In some embodiments, the tube bore is at least about 50 mm long. In some embodiments, the tube bore is at least about 100 mm long. In some embodiments, the tube bore is at least about 170 mm long. In some embodiments, the tube bore is at least about 300 mm long.

Optionally, an inside wall of the tube that defines the tapered tube bore extends at an angle, relative to a longitudinal axis of the tube, of less than about 2°. Optionally, a taper ratio of the tapered tube bore, calculated as a ratio of (a) a change in inside diameter of the tube bore to (b) length of the taper along a longitudinal axis of the tube is no greater than about 1:14.

Optionally, at 3206, a tubular sheath is disposed substantially coaxially with the proximal end of the tube bore. Optionally, at 3208, the crimped blood pump is translated from the proximal end of the tube bore to the tubular sheath, without substantially altering an outside dimension of the crimped blood pump.

Translating 3208 the crimped blood pump from the proximal end of the tube bore to the tubular sheath may include: (a) releasably restraining 3210 a distal end portion of the tubular sheath in a hub. The hub is attached to the proximal end of the tube. The hub defines a hub bore therethrough coaxial with the tube bore. One end of the hub bore is coupled to the proximal end of the tube bore. The other end of the hub bore is configured to receive the distal end portion of the tubular sheath substantially coaxially with the tube bore. Translating 3208 the crimped blood pump from the proximal end of the tube bore to the tubular sheath may also include: (b) translating 3212 the crimped blood pump through the hub bore. Optionally, the method further includes releasing 3214 the distal end portion of the tubular sheath from the hub.

Optionally, the method includes translating 3216 the crimped blood pump out of the tubular sheath and into a vasculature of a patient and allowing 3218 the crimped blood pump to resiliently expand within the vasculature.

Figure 33:
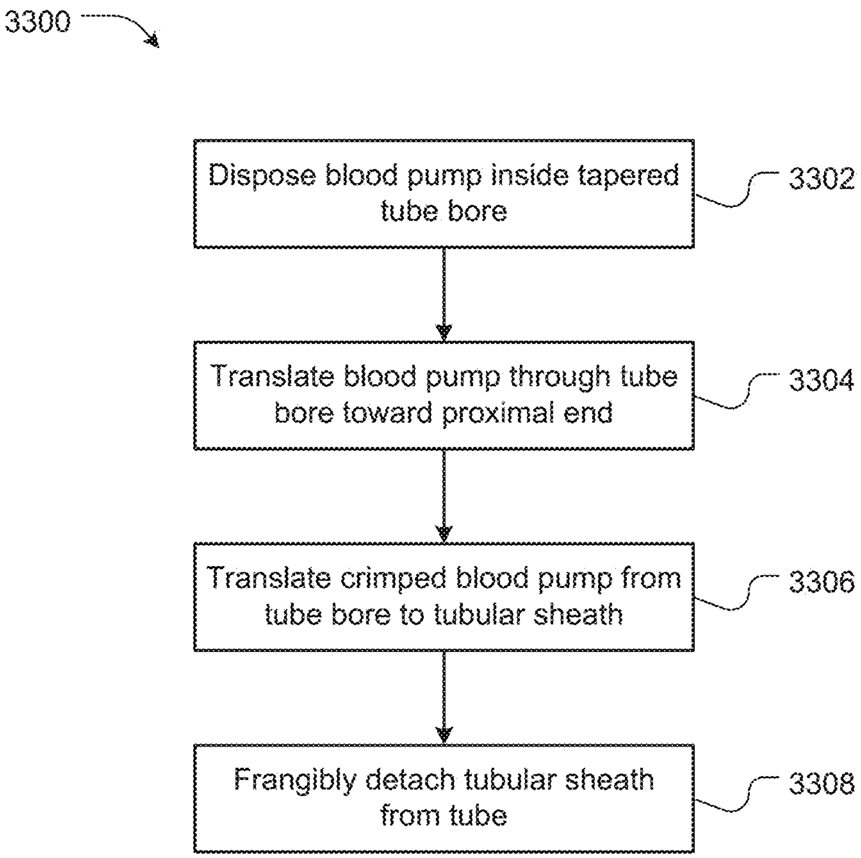

FIG. 33 is a flowchart that schematically illustrates another method 3300 for crimping a blood pump. The method 3300 may, for example, be practiced using the crimp tool 2802 described herein with respect to FIG. 28. The method 3300 includes disposing 3302 the blood pump inside a distal end of a tapered longitudinal tube bore. The tube bore is defined by an elongated tube. A proximal end of the tube is coaxially and frangibly attached to a distal end of a tubular sheath. The tubular sheath has an inside dimension. The tube bore is at least about 30 mm long. The tube bore has an inside dimension that tapers along the length of the tube bore from (a) at least about a maximum outside dimension of the blood pump at the distal end of the tube bore to (b) about the inside dimension of the tubular sheath at the proximal end of the tube bore.

At 3304, the blood pump is translated through the tube bore in a direction toward the proximal end of the tube bore, including contacting an outside surface of the blood pump with an inside surface of the elongated tube as the blood pump translates through the tube bore, thereby crimping the blood pump to produce a crimped blood pump. At 3306, the crimped blood pump is translated from the proximal end of the tube bore to the tubular sheath, without substantially altering an outside dimension of the crimped blood pump. At 3308, the tubular sheath is frangibly detached from the tube, with the crimped blood pump disposed within the tubular sheath.

Catheter Indicia

Figure 34:
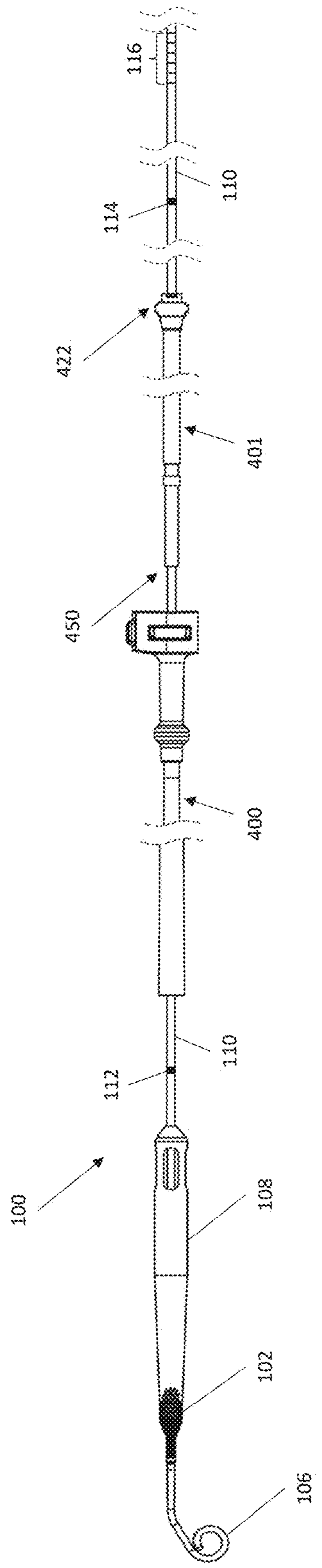
FIG. 34 is a side view of a blood pump with retraction indicia on a catheter associated therewith.

In some embodiments, one or more indicia may be provided on the catheter to assist with various aspects of crimping, inserting, positioning, and/or using a compressible and expandable blood pump system. FIG. 34 depicts an embodiment of a blood pump 100 that includes a retraction-indicia 112 on the catheter 110 that may aid during crimping of the blood pump via the crimp tool 400 and retraction of the crimped blood pump into the transfer sheath 401, as described herein.

For example, in some implementations, it may be difficult to determine whether the blood pump has been fully withdrawn into the transfer sheath (e.g., if the crimp tool 400 and/or transfer sheath 401 are opaque). In such an example, if the blood pump 100 is not retracted far enough, portions of the blood pump 100, such as the pigtail 106, may extend out of the transfer sheath 401 when it is disengaged from the crimp tool 400, which may interfere with the ability of the blood pump 100 to be inserted into an introducer, and/or may result in damage to the blood pump 100. Moreover, in some instances, the transfer sheath 401 may include one or more interior features that may damage the blood pump 100 if the blood pump 100 is withdrawn too far into the transfer sheath. Accordingly, the retraction indicia 112 may be positioned on the catheter 110 such that when the crimped blood pump is drawn into the transfer sheath 401 to the correct or desired position, the retraction indicia becomes exposed proximally of the proximal end 422 of the transfer sheath 401. As shown in FIG. 34, the retraction indicia 112 may include a band (e.g., a colored band extending around a circumference of the catheter). As will be appreciated, the indicia may include other suitable visual cues to the user to stop retracting the blood pump into the crimp tool and the transfer sheath. For example, the retraction indicia may include a picture or icon (e.g., a stop sign), or text (e.g., "STOP).

As described herein, a user may pull the blood pump 100 through the crimp tool 400 and transfer sheath 401 coupled to the crimp tool 400 to crimp the blood pump 100 and prepare the pump for insertion into a patient. During this process, seeing the retraction indicia 112 emerge from the proximal end 422 of the transfer sheath may provide a visual indication that the user should stop pulling and that the pump is properly received within the transfer sheath 401. Subsequently, the user may disengage the transfer sheath 401 from the crimp tool 400 and proceed with insertion of the crimped blood pump 100 into a patient via an introducer, as described above.

In view of the foregoing, the position of the retraction indicia 112 on the catheter 110 may be selected based on the dimensions of the blood pump 100 and transfer sheath 401. For example, the first indicia 112 may be located on the catheter 110 at a position corresponding to the length of the transfer sheath 401 such that when the blood pump is retracted into the transfer sheath, a distal end of the pigtail, which may be uncurled within the transfer sheath, is within the transfer sheath 401 and adjacent a distal end 450 of the transfer sheath. In some instances, the position of the retraction indicia 112 may be selected such that the distal end of the pigtail is spaced a predetermined distance (e.g., about 0.1 to about 5 cm) from the distal end 450 of the transfer sheath 401 when the retraction indicia is just visible outside of the proximal end 422 of the transfer sheath 401. However, it should be appreciated that the current disclosure is not limited to any particular spacing between the end of the pigtail 106 and the distal end 450 of the transfer sheath 401, and that the retraction indicia 112 may be positioned at any suitable location corresponding to a proper position of the crimped blood pump 100 within the transfer sheath 401.

Although the retraction indicia is described above as indicating a point when a user should stop retracting the blood pump 100 into the transfer sheath 401, other approaches may be suitable. For example, in some embodiments, the retraction indicia 112 may be arranged to indicate "safe zone" where the crimped blood pump 100 may be acceptably positioned within the transfer sheath 401, and a user may stop retracting the blood pump while any portion of the "safe zone" is visible outside of the proximal end 422 of the transfer sheath 401. In such an embodiment, the entirety of the "safe zone" becoming visible outside of the transfer sheath may indicate that the blood pump had been retracted too far.

In some embodiments, the "safe zone" may be formed as an elongated band on the catheter 110. The "safe zone" also may be formed via multiple bands extending along the catheter. In such embodiments, the elongate band or multiple bands may be the same color, or may have different colors. For example, in an illustrative embodiment, the elongate band may have red, yellow, and green colors (e.g., extending along a length of the safe zone and along a length of the catheter) to indicate to a user that they are approaching the end of the "safe zone" and that the user needs to stop pulling the catheter into the transfer sheath.

Referring again to FIG. 34, in some embodiments, the blood pump 100 may include an advancement indicia 114 that may aid during insertion of the crimped blood pump 100 through an introducer (not depicted) that is received in a patient's vasculature, as described above. For example, while the crimped blood pump 100 is advanced through an introducer, the crimped blood pump 100 may form a fluid tight seal within a lumen of the introducer. However, when the crimped blood pump 100 emerges from a distal end of the introducer and expands (which may be referred to as "hatching" of the pump housing including tubular mesh structure 102), the lumen of the introducer is no longer obstructed and blood may be able to flow back through the introducer, the transfer sheath 401, and out of the patient, thus leading to undesirable bleeding. Accordingly, the advancement indicia 114 may be provided on the catheter 110 at a location that indicates that the blood pump is about to emerge or has just emerged from the introducer (i.e., that the compressed blood pump is about to "hatch" or has just "hatched"). For example, the advancement indicia 114 may positioned on the catheter 110 such that when the advancement indicia 114 is adjacent the proximal end 422 of the transfer sheath 401, the compressed portion of the blood pump 100 that provides the sealing engagement with the interior of the introducer is about to emerge, or has just emerged, from the distal end of the introducer. This provides a visual indication that the user should disengage the transfer sheath 401 from the introducer such that one or more valves within a hub of the introducer sheath may seal onto the catheter 110 and provide hemostasis, thus avoiding bleeding. As described above, in some embodiments, the transfer sheath 401 may include features to allow it to be peeled away and removed from the catheter 110. In such embodiments, when a user sees that the advancement indicia 114 is about to be advanced into the proximal end 422 of the transfer sheath 410, the user may stop advancing the blood pump, disengage the transfer sheath 401 from the introducer, peel away the transfer sheath, and subsequently continue advancing the blood pump through the introducer.

In view of the foregoing, the position of the advancement indicia 112 on the catheter 110 may be selected based on the dimensions of the blood pump 100, transfer sheath 401, and introducer. For example, the advancement indicia 112 may be spaced proximally from tubular mesh 102 a distance along the catheter 110 corresponding to the combined length of the introducer and transfer sheath 401 when the transfer sheath is engaged with the introducer.

Similar to retraction indicia, the advancement indicia 112 may include a single band, an elongate band, multiple bands, or other suitable indicia to indicate when the user should disengage the transfer sheath from the introducer such that one or more valves within the hub of the introducer sheath may seal onto the catheter.

In some embodiments, a plurality of position indicia 116 also may be provided on the catheter 110, and may aid in assessing a position of the blood pump 100 when it is received in a patient. For example, the position indicia 116 may include a plurality of lines at predetermined intervals (e.g., 1 cm spacing, 2 cm spacing, or any other suitable spacing), and thus a user may be able to advance or retract the blood pump by a desired distance within the patient's vasculature by observing the position indicia 116 while advancing or retracting the blood pump. Moreover, in some instances, position indicia 116 may indicate an advantageous step distance that the catheter should be advanced when inserting the catheter through the transfer sheath and/or introducer. Such an advantageous step distance (e.g., about 2 cm) may be selected to avoid bending, buckling, kinking, or any other type of undesirable catheter deformation during advancement of the catheter.

It should be appreciated that the current disclosure is not necessarily limited to blood pumps that include indicia formed on the catheter 110, and that a blood pump may include any suitable combination of retraction indicia 112, advancement indicia 114, and/or placement indicia 116. Moreover, it should be understood that the various indicia may be formed on the catheter in any suitable manner, such as via pad printing with one or more colors that contrasts a color of the catheter 110, or etching (e.g., laser etching) to form a contrasting color and/or texture on the catheter 110. In some instances, the catheter may be formed from a different material and/or different colored material at the locations corresponding to the various indicia.

While the application describes exemplary embodiments, modifications to, and variations of, the illustrated embodiments may be made without departing from the inventive concepts disclosed herein. For example, although specific parameter values, such as numbers and shapes of pillars 1200 and 1202, lengths of tubes 404, inside and outside diameters, taper ratios and taper angles, may be recited in relation to disclosed embodiments, within the scope of the present disclosure, the values of all parameters may vary over wide ranges to suit different applications. Unless otherwise indicated in context, or would be understood by one of ordinary skill in the art, terms such as "about" mean within ±20%.

In most embodiments, including in the claims, the heart pump 100 and the tubular sheath, such as the tubular transfer sheath 401, are workpieces, relative to the crimp tool 400, and not elements of the crimp tool 400.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

As used herein, including in the claims, an element described as being configured to perform an operation "or" another operation is met by an element that is configured to perform only one of the two operations. That is, the element need not be configured to operate in one mode in which the element performs one of the operations, and in another mode in which the element performs the other operation. The element may, however, but need not, be configured to perform more than one of the operations.

Although aspects of embodiments may be described with reference to flowcharts and/or block diagrams, functions, operations, decisions, etc. of all or a portion of each block, or a combination of blocks, may be combined, separated into separate operations or performed in other orders. References to a "module," "operation," "step" and similar terms are for convenience and not intended to limit their implementation.

Disclosed aspects, or portions thereof, may be combined in ways not listed herein and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective pillars from one another and are not intended to indicate any particular order or total number of pillars in any particular embodiment. Thus, for example, a given embodiment may include only a second pillar and a third pillar.

What is claimed is:

1. A blood pump comprising:

an outflow tube comprising a first opening and a second opening, wherein the second opening comprises a notch that makes the second opening larger than the first opening; and an impeller and a mesh structure, the impeller held in the mesh structure, the blood pump being attached to a distal end of a catheter, wherein the outflow tube is collapsible and the outflow tube is coupled to the mesh structure such that, during operation of the blood pump, blood flows into the mesh structure and into an interior of the outflow tube and the blood flows out of the outflow tube through the first and second openings of the outflow tube.

2. The blood pump of claim 1, wherein the notch extends proximally.

3. The blood pump of claim 1, wherein a distal end of the outflow tube is disposed over a proximal portion of the mesh structure such that the proximal portion of the mesh structure is disposed within an interior of the outflow tube.

4. The blood pump of claim 3, wherein the first and second openings of the outflow tube are disposed on a proximal portion of the outflow tube.

5. The blood pump of claim 4, wherein, during operation of the blood pump, blood flows into a distal portion of the mesh structure and into the interior of the outflow tube and the blood flows out of the outflow tube through the first and second openings of the outflow tube.

6. The blood pump of claim 1, wherein the outflow tube is collapsible.

7. The blood pump of claim 1, wherein the impeller is radially compressible.

8. The blood pump of claim 1, wherein the mesh structure is radially compressible.

9. The blood pump of claim 1, wherein the mesh structure is made of a memory material.

10. The blood pump of claim 9, wherein the memory material is nitinol.

11. A blood pump comprising:

an outflow tube comprising a first opening and a second opening, wherein the second opening is larger than the first opening and extends further than the first opening in a proximal direction; and an impeller and a mesh structure, the impeller held in the mesh structure, the blood pump being attached to a distal end of a catheter, wherein the outflow tube is collapsible and the outflow tube is coupled to the mesh structure such that, during operation of the blood pump, blood flows into the mesh structure and into an interior of the outflow tube and the blood flows out of the outflow tube through the first and second openings of the outflow tube.

12. The blood pump of claim 11, wherein the second opening comprises a proximally-extending notch.

13. The blood pump of claim 11, wherein a distal end of the outflow tube is disposed over a proximal portion of the mesh structure such that the proximal portion of the mesh structure is disposed within an interior of the outflow tube.

14. The blood pump of claim 13, wherein the first and second openings of the outflow tube are disposed on a proximal portion of the outflow tube.

15. The blood pump of claim 14, wherein, during operation of the blood pump, blood flows into a distal portion of the mesh structure and into the interior of the outflow tube and the blood flows out of the outflow tube through the first and second openings of the outflow tube.

16. The blood pump of claim 11, wherein the impeller is radially compressible.

17. The blood pump of claim 11, wherein the mesh structure is radially compressible.

18. The blood pump of claim 11, wherein the mesh structure is made of a memory material.

19. The blood pump of claim 18, wherein the memory material is nitinol.

* * * * *